US009340593B2

(12) United States Patent
Wong et al.

(10) Patent No.: US 9,340,593 B2
(45) Date of Patent: May 17, 2016

(54) METHOD OF TREATING DIABETES BY A CTRP12 POLYPEPTIDE

(75) Inventors: Guang William Wong, Lutherville, MD (US); Zhikui Wei, Baltimore, MD (US); Jonathan M. Peterson, Parkville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/111,003

(22) PCT Filed: Apr. 11, 2012

(86) PCT No.: PCT/US2012/033015
§ 371 (c)(1),
(2), (4) Date: Jan. 24, 2014

(87) PCT Pub. No.: WO2012/142083
PCT Pub. Date: Oct. 18, 2012

(65) Prior Publication Data
US 2014/0147421 A1     May 29, 2014

Related U.S. Application Data

(60) Provisional application No. 61/474,220, filed on Apr. 11, 2011.

(51) Int. Cl.
*A61K 38/00* (2006.01)
*C07K 14/47* (2006.01)
*A61K 48/00* (2006.01)
*A61K 31/7088* (2006.01)
*A61K 31/7105* (2006.01)
*A61K 38/19* (2006.01)

(52) U.S. Cl.
CPC .............. *C07K 14/47* (2013.01); *A61K 31/7088* (2013.01); *A61K 31/7105* (2013.01); *A61K 38/191* (2013.01); *A61K 48/005* (2013.01); *C12N 2710/10341* (2013.01); *G01N 2500/04* (2013.01); *G01N 2500/10* (2013.01)

(58) Field of Classification Search
CPC ........ C07K 14/47; C07K 14/07; C07K 14/08; C07K 14/16
See application file for complete search history.

(56) References Cited

U.S. PATENT DOCUMENTS

2005/0266464 A1   12/2005   Marshall et al.
2008/0287358 A1*  11/2008   Noelle et al. .................... 514/12
2011/0021422 A1    1/2011   Tennenbaum et al.

FOREIGN PATENT DOCUMENTS

KR   10-0803175 B1    2/2008
WO   2005/042576 A1   5/2005

OTHER PUBLICATIONS

Yamauchi et al., Nature Med. 8: 941-946, 2001.*
Kim, et al. "Tumor necrosis factor-alpha and interleukin-1beta increases CTRP1 expression in adipose tissue", FEBS Letters, vol. 580, pp. 3953-3960 (2006).
Enomoto, T., et al., "Adipolin/C1qdc2/CTRP12 protein functions as an adipokine that improves glucose metabolism", The Journal of Biological Chemistry, Oct. 7, 2011, vol. 286, No. 40, pp. 34552-34558.
Peterson, J., et al., "C1q/TNF-related protein-3 (CTRP3), a novel adipokine that regulates hepatic glucose output", The Journal of Biological Chemistry, Dec. 17, 2010, vol. 285, No. 51, pp. 39691-39701.
Wei, Z., et al., "Metabolic regulation by C1q/TNF-related protein-13 (CTRP13)", the Journal of Biological Chemistry, May 6, 2011, vol. 286, No. 18, pp. 15652-15665.
Wei, Z., et al., "C1q/TNF-related protein-12 CTRP12) a novel adipokine that improves insulin sensitivity and glycemic control n mouse models of obesity and diabetes", The Journal of Biological Chemistry, Mar. 23, 2012, vol. 287, No. 13, pp. 10301-10115.
Wong, G., et al., "Molecular, biochemical and functional characterizations of C1q/TNF family members: adipose-tissue-selective expression patterns, regulation by PPAR-y agonist, cysteine-mediated oligomerizations, combinatorial associations and metabolic functions", Biochem. J. (2008) vol. 416, pp. 161-177.
EPO search report dated Nov. 19, 2014 for EP application 12771031.7.
Gene Sequence Database, Apr. 17, 2007, Accession No. Q8R2Z0.
Gene Sequence Database, Dec. 28, 2006, Accession No. AEL62544.

* cited by examiner

*Primary Examiner* — Gyan Chandra
(74) *Attorney, Agent, or Firm* — JHU Technology Ventures

(57) ABSTRACT

The present invention provides substantially purified peptide portions of adipokine polypeptides, including, for example, C1q/TNF-related protein-12 (CTRP12), a functional homolog or function fragment of CTRP12, and a fusion polypeptide comprising any of the above. Methods for treating Type 2 diabetes mellitus by administering to a patient any of the following; CTRP12, a functional homolog of CTRP12, a functional fragment of CTRP12 or its functional homolog, a fusion polypeptide comprising any of the above, a substantially purified nucleic acid molecule encoding a polypeptide of any of the above, a vector comprising such nucleic acid molecule, a host cell transformed with such vector, a ligand that specifically binds to a polypeptide mentioned above, a compound that modifies the level of expression or activity of the amino acid sequence according to any of the above, a pharmaceutical composition comprising any one the above and a pharmaceutically acceptable carrier, and any combination of the above are also provided.

2 Claims, 21 Drawing Sheets

SEQUENCE LISTING

```
<160> NUMBER OF SEQ ID NOS: 44

<210> SEQ ID NO 1
<211> LENGTH: 302
<212> TYPE: PRT
<213> ORGANISM: homo sapiens
```

```
<400> SEQUENCE: 1

Met Arg Arg Trp Ala Trp Ala Ala Val Val Leu Leu Gly Pro Gln
1               5                   10                  15

Leu Val Leu Leu Gly Gly Val Gly Ala Arg Arg Glu Ala Gln Arg Thr
            20                  25                  30

Gln Gln Pro Gly Gln Arg Ala Asp Pro Pro Asn Ala Thr Ala Ser Ala
                35                  40                  45

Ser Ser Arg Glu Gly Leu Pro Glu Ala Pro Lys Pro Ser Gln Ala Ser
    50                  55                  60

Gly Pro Glu Phe Ser Asp Ala His Met Thr Trp Leu Asn Phe Val Arg
65                  70                  75                  80

Arg Pro Asp Asp Gly Ala Leu Arg Lys Arg Cys Gly Ser Arg Asp Lys
                85                  90                  95

Lys Pro Arg Asp Leu Phe Gly Pro Pro Gly Pro Pro Gly Ala Glu Val
                100                 105                 110

Thr Ala Glu Thr Leu Leu His Glu Phe Gln Glu Leu Leu Lys Glu Ala
                115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
                180                 185                 190

Ala Ser Gly Arg Phe Thr Ala Pro Val Ser Gly Ile Phe Gln Phe Ser
    195                 200                 205

Ala Ser Leu His Val Asp His Ser Glu Leu Gln Gly Lys Ala Arg Leu
210                 215                 220

Arg Ala Arg Asp Val Val Cys Val Leu Ile Cys Ile Glu Ser Leu Cys
225                 230                 235                 240

Gln Arg His Thr Cys Leu Glu Ala Val Ser Gly Leu Glu Ser Asn Ser
                245                 250                 255

Arg Val Phe Thr Leu Gln Val Gln Gly Leu Gln Leu Gln Ala Gly
    260                 265                 270

Gln Tyr Ala Ser Val Phe Val Asp Asn Gly Ser Gly Ala Val Leu Thr
    275                 280                 285

Ile Gln Ala Gly Ser Ser Phe Ser Gly Leu Leu Gly Thr
    290                 295                 300

<210> SEQ ID NO 2
<211> LENGTH: 308
<212> TYPE: PRT
<213> ORGANISM: Mus musculus

<400> SEQUENCE: 2

Met Trp Ala Trp Gly Trp Ala Ala Ala Leu Leu Trp Leu Gln Thr
1               5                   10                  15

Ala Gly Ala Gly Ala Arg Gln Glu Leu Lys Lys Ser Arg Gln Leu Phe
            20                  25                  30

Ala Arg Val Asp Ser Pro Asn Ile Thr Thr Ser Asn Arg Glu Gly Phe
                35                  40                  45

Pro Gly Ser Val Lys Pro Pro Glu Ala Ser Gly Pro Glu Leu Ser Asp
    50                  55                  60
```

Ala His Met Thr Trp Leu Asn Phe Val Arg Arg Pro Asp Asp Gly Ser
 65                  70                  75                  80

Ser Arg Lys Arg Cys Arg Gly Arg Asp Lys Lys Ser Arg Gly Leu Ser
                 85                  90                  95

Gly Leu Pro Gly Pro Pro Gly Pro Pro Gly Pro Pro Gly Pro Pro Gly
            100                 105                 110

Ser Pro Gly Val Gly Val Thr Pro Glu Ala Leu Leu Gln Glu Phe Gln
        115                 120                 125

Glu Ile Leu Lys Glu Ala Thr Glu Leu Arg Phe Ser Gly Leu Pro Asp
    130                 135                 140

Thr Leu Pro Gln Glu Pro Ser Gln Arg Leu Val Val Glu Ala Phe
145                 150                 155                 160

Tyr Cys Arg Leu Lys Gly Pro Val Leu Val Asp Lys Lys Thr Leu Val
                165                 170                 175

Glu Leu Gln Gly Phe Gln Ala Pro Thr Thr Gln Gly Ala Phe Leu Arg
            180                 185                 190

Gly Ser Gly Leu Ser Leu Ser Leu Gly Arg Phe Thr Ala Pro Val Ser
        195                 200                 205

Ala Ile Phe Gln Phe Ser Ala Ser Leu His Val Asp His Ser Glu Leu
    210                 215                 220

Gln Gly Arg Gly Arg Leu Arg Thr Arg Asp Met Val Arg Val Leu Ile
225                 230                 235                 240

Cys Ile Glu Ser Leu Cys His Arg His Thr Ser Leu Glu Ala Val Ser
                245                 250                 255

Gly Leu Glu Ser Asn Ser Arg Val Phe Thr Val Gln Val Gln Gly Leu
            260                 265                 270

Leu His Leu Gln Ser Gly Gln Tyr Val Ser Val Phe Val Asp Asn Ser
        275                 280                 285

Ser Gly Ala Val Leu Thr Ile Gln Asn Thr Ser Ser Phe Ser Gly Met
    290                 295                 300

Leu Leu Gly Thr
305

<210> SEQ ID NO 3
<211> LENGTH: 308
<212> TYPE: PRT
<213> ORGANISM: Equus caballus

<400> SEQUENCE: 3

Met Arg Trp Ala Trp Ala Ala Ala Leu Ala Leu Leu Trp Pro Gln Leu
1               5                   10                  15

Ala Leu Leu Gly Gly Val Gly Ala Arg Arg Glu Ser Lys Arg Pro Arg
                20                  25                  30

Gln Pro Gly Gln Arg Thr Glu Ser Pro Asn Ala Thr Val Ser Asn Ser
            35                  40                  45

Glu Gly Leu Pro Ala Ser Pro Lys Leu Pro Glu Ala Leu Gly Pro Glu
        50                  55                  60

Phe Ser Asp Ala His Met Thr Trp Leu Asn Phe Val Arg Arg Pro Asp
65                  70                  75                  80

Asp Gly Val Ser Lys Lys Arg Cys Arg Gly Gln Asn Lys Lys Leu Arg
                85                  90                  95

Gly Leu Ser Gly Pro Pro Gly Pro Pro Gly Pro Pro Gly Pro Pro Gly
            100                 105                 110

Pro Pro Gly Ala Glu Ile Thr Gln Glu Ala Leu Leu Arg Glu Phe Gln
        115                 120                 125

```
Glu Met Leu Lys Glu Ala Thr Glu Arg Arg Phe Ser Gly Leu Leu Gly
            130                 135                 140

Pro Leu Pro Glu Gly Thr Gly Glu Arg Leu Val Ala Glu Gly Phe
145                 150                 155                 160

His Cys Gln Leu Lys Gly Pro Met Arg Val Asp Lys Lys Thr Leu Val
                165                 170                 175

Glu Leu His Asp Phe Gln Ala Pro Thr Ala Gln Gly Ala Phe Leu Arg
            180                 185                 190

Gly Ser Gly Leu Ser Leu Ala Ser Gly Arg Phe Thr Ala Pro Val Ser
        195                 200                 205

Ala Ile Phe Gln Phe Ser Ala Ser Leu His Val Asp His Arg Glu Leu
210                 215                 220

Gln Gly Arg Gly Gln Leu Arg Ala Arg Asp Thr Val Arg Ala Leu Ile
225                 230                 235                 240

Cys Ile Glu Ser Leu Cys His Arg His Thr Ser Leu Glu Ala Ile Ser
                245                 250                 255

Gly Leu Glu Ser Asn Gly Arg Val Phe Thr Val His Val Gln Gly Leu
            260                 265                 270

Leu Glu Leu Gln Ala Gly Gln Tyr Thr Ser Val Phe Val Asp Asn Gly
        275                 280                 285

Ser Gly Ala Ala Leu Thr Val Gln Ser Ser Ser Phe Ser Gly Leu
290                 295                 300

Leu Leu Gly Met
305

<210> SEQ ID NO 4
<211> LENGTH: 298
<212> TYPE: PRT
<213> ORGANISM: G. gallus

<400> SEQUENCE: 4

Met Ala Ala Lys Lys Glu Arg Lys Ile Lys Lys Glu Pro Asn Gln Tyr
1               5                   10                  15

Thr Glu Pro Phe Asn Ala Thr Leu Ser Asn Ser Glu Glu Leu His Gly
            20                  25                  30

His Pro Lys Ile Leu Glu Ser Pro Asp Pro Arg Ile Thr Asp Pro Arg
        35                  40                  45

Arg Thr Trp Ile Ser Phe Val His Arg Pro Asp Asp Gly Asn Thr Ser
50                  55                  60

Lys Arg Lys Cys Lys Gly Lys Asp Lys Lys Leu Arg Gly Leu Val Gly
65                  70                  75                  80

Pro Pro Gly Pro Pro Gly Pro Gln Gly Pro Pro Gly Ala Pro Gly Ala
                85                  90                  95

Glu Val Thr Arg Glu Val Leu Leu Gln Glu Phe Lys Glu Ile Leu Lys
            100                 105                 110

Glu Ala Ile Glu Arg Arg Ala Ser Leu Ala Ile Ser Ala His Pro Ser
        115                 120                 125

Gln Leu Pro Pro Leu Leu Leu Ser Leu Glu Glu Val Ser Pro Tyr Arg
130                 135                 140

Arg Val Glu Glu Ala Phe His Cys Lys Leu Lys Gly Gln Val Val Val
145                 150                 155                 160

Asp Lys Lys Thr Leu Val Glu Leu Gln Asn Phe Gln Ser Pro Leu Ala
                165                 170                 175

Lys Gly Ala Phe Leu Arg Gly Thr Gly Leu Asn Leu Ala Thr Gly Arg
            180                 185                 190
```

```
Phe Thr Ala Pro Val Ser Gly Ile Tyr Gln Phe Ser Ala Asn Val His
        195                 200                 205

Ile Asp His Ser Glu Leu Lys Ser Lys Val Gln Leu Arg Ala Arg Asp
    210                 215                 220

Asn Val Arg Val Leu Ile Cys Ile Glu Ser Leu Cys His Arg Tyr Thr
225                 230                 235                 240

Ser Leu Glu Val Ile Ala Gly Leu Glu Ser Asn Ser Lys Ile Phe Thr
            245                 250                 255

Val Tyr Val His Gly Leu Leu Gln Leu Gln Ala Gly Gln Tyr Thr Ser
                260                 265                 270

Ile Phe Val Asp Asn Ser Ala Gly Ala Pro Ile Thr Ile Gln Asn Gly
            275                 280                 285

Ser Asp Phe Met Gly Met Leu Met Gly Ala
        290                 295

<210> SEQ ID NO 5
<211> LENGTH: 324
<212> TYPE: PRT
<213> ORGANISM: Xenopus tropicalis

<400> SEQUENCE: 5

Met Arg Cys Trp Val Trp Leu Leu Val Ala Ile Val Leu Cys Gln Gln
1               5                   10                  15

Leu Ser Val Val Arg Val Leu Ala Ala Lys Lys Glu Arg Lys Lys Gly
            20                  25                  30

Lys Asp Pro His Gln Phe Thr Glu Pro Phe Asn Val Ser Leu Ser Asn
        35                  40                  45

Ser Glu Glu Leu His Glu Thr Asp Lys Leu Ser Glu Thr Pro Asp Pro
    50                  55                  60

Gly Leu Pro Asp Ala Tyr Thr Thr Trp Leu Gly Phe Val Gly Arg Thr
65                  70                  75                  80

Asp Asp Gly Ala Asn Ser Lys Lys Lys Cys Lys Gly Lys Asp Lys Lys
                85                  90                  95

Leu Arg Gly Leu Phe Gly Pro Pro Gly Pro Pro Gly Pro Gln Gly Pro
            100                 105                 110

Pro Gly Pro Pro Gly Met Pro Gly Ala Glu Val Thr Tyr Glu Val Leu
        115                 120                 125

Leu Gln Asp Phe Lys Gln Met Leu Lys Glu Ala Thr Glu Arg Arg Leu
    130                 135                 140

Met Ser Gly Asp Ile Pro Glu His Thr Ser Glu Leu Pro Pro Ile Val
145                 150                 155                 160

Leu Pro Val Glu Asp Leu Ser Pro Tyr Arg Arg Val Asp Glu Gly Phe
                165                 170                 175

His Cys Arg Leu Lys Gly Gln Val Ile Val Asp Lys Lys Thr Leu Val
            180                 185                 190

Glu Leu Gln Asn Phe Gln Met Pro Thr Ala Lys Gly Ser Phe Leu Arg
        195                 200                 205

Gly Ser Gly Leu Asn Leu Ala Thr Gly Arg Phe Thr Ala Ser Val Pro
    210                 215                 220

Gly Ile Tyr Gln Phe Ser Ala His Val His Ile Asp His Ser Glu Ile
225                 230                 235                 240

Lys Ser Lys Ala Gln Leu Arg Pro Arg Asp Asn Val Arg Val Leu Ile
                245                 250                 255

Cys Ile Glu Ser Met Cys His Arg Tyr Thr Ser Leu Glu Val Ile Ala
            260                 265                 270
```

```
Gly Leu Glu Ser Asn Ser Lys Ile Phe Thr Val His Val Gln Gly Leu
            275                 280                 285

Leu Gln Leu Gln Val Gly Gln Tyr Thr Ser Ile Phe Val Asp Asn Ser
        290                 295                 300

Ala Gly Ala Pro Ile Thr Val Gln Asn Gly Ser Asp Phe Met Gly Ile
305                 310                 315                 320

Leu Met Gly Leu

<210> SEQ ID NO 6
<211> LENGTH: 318
<212> TYPE: PRT
<213> ORGANISM: Danio rerio

<400> SEQUENCE: 6

Met Arg Cys Trp Val Leu Ala Val Val Thr Ala Val Leu Trp Ser Gln
1               5                   10                  15

Cys Ile Pro Leu Gly Trp Ala Glu Gly Arg Lys Val Pro Lys Arg Leu
            20                  25                  30

Lys Glu Gly Ala Pro Gln His Thr Glu Ala Phe Asn Thr Thr Leu Ser
        35                  40                  45

Asn Ser Glu Glu Leu Asp Gly Ser Pro Lys Gln Val Gly Glu Asn Gln
50                  55                  60

Arg Val Asp Pro Leu Gly Ser Trp Met Asp Phe Val Lys Arg Pro Val
65                  70                  75                  80

Gly Asn Phe Pro Gly Lys Cys Arg Lys Arg Lys Arg Pro Leu Pro Gly
                85                  90                  95

Pro Pro Gly Pro Pro Gly Pro Pro Gly Pro Gln Gly Pro Pro Gly Ala
            100                 105                 110

Pro Gly Ala Glu Val Thr Gln Glu Val Leu Leu Arg Glu Phe Lys Glu
        115                 120                 125

Met Ile Lys Glu Ala Thr Glu Arg Arg Ala Ala Val Asp Arg Pro Ser
130                 135                 140

Glu Pro Ser Gln Leu Pro Thr Ala Leu Ile Thr Leu Glu Gly Met Thr
145                 150                 155                 160

Ser Tyr Arg Arg Ile Glu Glu Ala Phe His Cys Lys Leu Lys Gly Pro
                165                 170                 175

Val Val Val Asp Lys Lys Thr Leu Ala Glu Leu Gln Asn Phe Gln Thr
            180                 185                 190

Pro Pro Ala Lys Gly Ala Phe Leu Arg Gly Thr Gly Met Asp Gln Ser
        195                 200                 205

Thr Gly Arg Phe Thr Ala Pro Val Thr Gly Ile Tyr Gln Phe Ser Ala
210                 215                 220

Asn Val His Ile Asp His Thr Glu Val Lys Arg Ser Lys Ser Gln Leu
225                 230                 235                 240

Arg Ala Arg Asp Asn Val Arg Val Leu Ile Cys Ile Glu Ser Leu Cys
                245                 250                 255

His Arg Tyr Thr Ser Leu Glu Met Ile Val Gly Leu Glu Ser Asn Ser
            260                 265                 270

Lys Ile Phe Thr Val Ser Val His Gly Leu Leu Glu Leu Gln Ala Gly
        275                 280                 285

Gln Tyr Thr Ser Ile Phe Val Asp Asn Ala Ala Gly Ala Ser Ile Thr
        290                 295                 300

Ile Gln Asn Gly Ser Asp Phe Met Gly Met Leu Leu Gly Val
305                 310                 315
```

```
<210> SEQ ID NO 7
<211> LENGTH: 1055
<212> TYPE: DNA
<213> ORGANISM: Homo sapiens

<400> SEQUENCE: 7
ctcgccgcgc tgagccgcct cgggacggag ccatgcggcg ctgggcctgg gccgcggtcg      60
tggtcctcct cgggccgcag ctcgtgctcc tcggggggcgt cggggcccgg cgggaggcac    120
agaggacgca gcagcctggc cagcgcgcag atccccccaa cgccaccgcc agcgcgtcct    180
cccgcgaggg gctgcccgag gcccccaagc catcccaggc tcaggacct gagttctccg    240 acgcccacat gacatggctg aactttgtcc ggcggccgga cgacggcgcc ttaaggaagc    300
ggtgcggaag cagggacaag aagccgcggg atctcttcgg tcccccagga cctccaggtg    360
cagaagtgac cgcggagact ctgcttcacg agtttcagga gctgctgaaa gaggccacgg    420
agcgccggtt ctcagggctt ctggaccgc tgctgcccca ggggcgggc ctgcggctgg     480 tgggcgaggc ctttcactgc cggctgcagg tccccgccg gtggacaag cggacgctgg     540 tggagctgca tggtttccag gctcctgctg cccaaggtgc cttcctgcga ggctccggtc    600
tgagcctggc ctcgggtcgg ttcacggccc ccgtgtccgg catcttccag ttctctgcca    660
gtctgcacgt ggaccacagt gagctgcagg gcaaggcccg gctgcgggcc cgggacgtgg    720
tgtgtgttct catctgtatt gagtccctgt gccagcgcca cacgtgcctg gaggccgtct    780
caggcctgga gagcaacagc agggtcttca cgctacaggt gcaggggctg ctgcagctgc    840
aggctggaca gtacgcttct gtgtttgtgg acaatggctc cggggccgtc ctcaccatcc    900
aggcgggctc cagcttctcc gggctgctcc tgggcacgtg agggcgccca ggggggctgg    960
cgaggagctg ccgccggatc ccggggaccc tcctactgat gcccgtggtc accacaataa   1020
agagccctcc accctcaaaa aaaaaaaaaa aaaaa                               1055

<210> SEQ ID NO 8
<211> LENGTH: 927
<212> TYPE: DNA
<213> ORGANISM: Mus musculus

<400> SEQUENCE: 8
atgtgggcct ggggctgggc cgctgcagcg ctcctctggc tacagactgc aggagccggg      60
gcccggcagg agctcaagaa gtctcggcag ctgtttgcgc gtgtggattc ccccaatatt    120
accacgtcca accgtgaggg attcccaggc tccgtcaagc ccccggaagc ctctggacct    180
gagctctcag atgcccacat gacgtggttg aactttgtcc gacggccaga tgatgggtcc    240
tctagaaaac ggtgtcgtgg ccgggacaag aagtcgcgag gcctctcagg tctcccaggg    300 ccccaggac ctcctggccc tcctggtccc cctggctccc ctggtgtggg cgttacccca    360
gaggccttac tgcaggaatt tcaggagata ctgaaagagg ccacagaact tcgattctca    420
gggctaccag acacattgtt accccaggaa cccagccaac ggctggtggt tgaggccttc    480
tactgccgtt tgaaaggccc tgtgctggtg acaagaaga ctctggtgga actgcaagga    540
ttccaagctc ctactactca gggcgccttc tgcggggat ctggcctgag cctgtccttg    600
ggccgattca cagccccagt ctctgccatc ttccagtttt ctgccagcct gcacgtggac    660
cacagtgaac tgcagggcag aggccggttg cgtacccggg atatggtccg tgttctcatc    720
tgtattgagt ccttgtgtca tcgtcatacg tccctggagg ctgtatcagg tctggagagc    780
aacagcaggg tcttcacagt gcaggttcag gggctgctgc atctacagtc tggacagtat    840
```

| | |
|---|---|
| gtctctgtgt tcgtggacaa cagttctggg gcagtcctca ccatccagaa cacttccagc | 900 |
| ttctcgggaa tgcttttggg tacctag | 927 |

```
<210> SEQ ID NO 9
<211> LENGTH: 1071
<212> TYPE: DNA
<213> ORGANISM: Equus caballas

<400> SEQUENCE: 9
```

| | |
|---|---|
| cagacatgca ccggccaggc gccccccgag gccacgtccc cgcgcaaggg ccctgagtgc | 60 |
| cggctgtgcc accgccccca tgagcgcgcc tgggtgcccc tgcttgcagc gctgagccgc | 120 |
| ctaggtccgg agccgccgga cgccatgcgc tgggcctggg ccgcggccct ggccctcctc | 180 |
| tggccgcagc tcgcgctcct cggggggcgtc ggggctcgac gggagtccaa gaggccgcgg | 240 |
| cagccgggcc agcgcaccga gtccccgaac gccaccgtgt ccaacagcga ggggctgccg | 300 |
| gcctccccca agtccctga ggccttgggg cctgagttct cagatgccca catgacgtgg | 360 |
| ctgaacttcg tccggcggcc ggatgatggg gtctcaaaga aacgatgccg aggccagaac | 420 |
| aaaaagttgc gaggcctctc cggccccccca gggcctcctg gccccctgg cccccaggc | 480 |
| cccccggtg cggaaatcac tcaggaggcc ctgctgaggg agtttcagga gatgctgaaa | 540 |
| gaagccaccg agcgtcggtt ctcggggctg ctgggcccgt tgctacccga ggggacaggc | 600 |
| gagcggctgt tggccgaggg cttccactgc cagctgaagg gccccatgcg ggtggacaag | 660 |
| aagactctgg tagagctgca tgacttccag gctcctacag cccagggcgc cttcctgcgg | 720 |
| gggtccggcc tgagcctcgc ctcgggccgg tttacagccc cagtgagcgc cattttccag | 780 |
| ttctctgcca gcctgcatgt agaccacagg gagctgcagg gcaggggtca gctgcgggcc | 840 |
| cgggacacag tgcgggcact catctgcatc gagtccctgt gccatcgcca cacgtccctg | 900 |
| gaggccatct caggcctaga gagcaatggc agggtcttca cggtgcacgt gcaggggctg | 960 |
| ctggagctgc aggctggaca gtacacctcc gtcttcgtgg acaatggctc cggggcggcc | 1020 |
| ctcaccgtcc agagcagctc cagcttctct ggcctgctcc tgggcatgtg a | 1071 |

```
<210> SEQ ID NO 10
<211> LENGTH: 2174
<212> TYPE: DNA
<213> ORGANISM: G. gallus

<400> SEQUENCE: 10
```

| | |
|---|---|
| atggcagcaa agaaagagag aaagataaag aaagaaccca atcagtacac agagcctttc | 60 |
| aatgccaccc tatccaacag cgaggagctg cacgggcatc ccaagatcct cgaatctcca | 120 |
| gaccctcgaa tcacagatcc acggcggacc tggatctcct tgtccaccg cccagatgat | 180 |
| ggcaacacct ctaaaaggaa atgcaaaggc aaagacaaga aattacgtgg tcttgttggg | 240 |
| cctccagggc ctcctggtcc ccagggtccc caggagcac tggtgctga agtcacccgg | 300 |
| gaagtcctgc tgcaggagtt taaggagata ttaaagaag ccattgagcg tcgggcatcc | 360 |
| ttggcaattt cagcacatcc cagccagctg cctccactcc tgctctcctt ggaggaagtt | 420 |
| tcaccctata gacgtgtaga ggaggcgttc cactgcaagc taaaaggaca agttgtcgtg | 480 |
| gataaaaaga ccctggtaga acttcagaac ttccagtcgc ctttggccaa aggagctttt | 540 |
| ctgcggggga cggggttaaa cctggcaacg ggacgtttca cagcacccgt atccggcatc | 600 |
| taccagttct cagccaacgt ccacatcgat catagtgagt tgaagagcaa agtccagctc | 660 |
| cgtgccagag ataacgtccg agtgttgatc tgcattgaat ctctctgcca ccgatacacg | 720 |

```
tctttggagg ttattgctgg tttggaaagt aacagcaaga tcttcactgt ctacgtgcat        780
ggcttgctgc agctgcaggc tggccagtac acctccatct ttgtggacaa cagtgctgga        840
gctcccatca ccattcagaa tggatccgat tcatgggca tgttaatggg cgcgtagcat         900
cgtctgcagc actgcagcag ggaagaacac gagttacagc cttacaacat atatttgact        960
gaagaaacct ttactttgac tcttgaagac cgcttcatgt aactgttggc atcttcttaa       1020
acaagcaaag agccttttcct cttgcagata cttcagcttg ctttcagagg ctgctgcttc      1080
tcaaggtcca caccagttca ttcaccttaa aaaaaaaaaa aaaatacact tttctaactc       1140
agaaacaaac tctgtaatat ttaatatgtg cttcaccgaa cagtacactg agatttggca       1200
tttgttgtaa tgttacttca cacgattaca cttgtaatta gcatgtcttt ggggctgatt       1260
gcgggctgtt taagtttgta atgaaggat tgagagggga agtaaaacag tgactgtgtt       1320
ccatgtgttg tggaggaagg agacaagaat ttgtcagcaa aactgttttt cacacaattg       1380
tgaatggtgt agggccctct ctcatgttca gactgagata cgtttgacaa gtagcatgtt       1440
gaattctcaa gcagtgcctg ttttcaaaga caggaatcca agggttgaac tgtttaacgg       1500
tggttcccta aatctaagta tgtttctctg atcttactga tgaagccaaa tacctcgctg       1560
cctgcacagt tttattttta tgaaaacgta aggccaatgg caccagttct agcatgaact       1620
ccctcagtta tgttcttatg ttttagtaag acatatactt ggctctggac tgcatcacat       1680
acacggcatc ctctcaggtg tcatatatcc gtttgtagat ctgtctgatg cgttttgcca       1740
gttgtgggtg ttgtcatttc actgggtttt tcccttcaag agacacttgg cctttaatg        1800 atgcaactta actaaggaaa tggctgttca gcagttcat agaaagatgg cagcggggcc        1860
ccagttggag tccggatact tttcttgaac atctgcagta aatggaggat ctccattgct       1920
tgacatttca attttttcat gatccattac aacaccttca taaaacgaga accaagactg       1980
ctggggacag cagaaggtgt gaaaaagtga gacagcagtt caccacagta gtgtttgttg       2040
gggcttcaca aagtgtgtaa ctcacatgaa gatcattaaa ccctaccaac aaggactggc       2100
tgtttacatt gggttttggt ggagtaggtg tagtcagggc acatggcctg tatcccagta       2160
tgtattacta tact                                                         2174
```

<210> SEQ ID NO 11
<211> LENGTH: 1919
<212> TYPE: DNA
<213> ORGANISM: Xenopus tropicalis

<400> SEQUENCE: 11

```
gatgctgccc tgatacttca gactttacag gcttcatagc tcagtgagtt ttaattacac         60
tttatggact tctgagcaag tcgataggag agaatttgtt ttcaacccat ccttttatgc        120
ggagaaagac ctggtgggat taatttatgc tttatctcaa cccttttgtc ttggccagtc        180
tgtatctaca ctgaaggagc tattctttcc acttgttttg tcctgttaag catcttgaa        240 agatacctgg agtgctttcc agctcagctt tctaactcct gaaggatata tttcccagaa        300
cataatgagg tgttgggtat ggctgttagt ggccatagtt ctgtgccagc agctttctgt       360
cgttcgagtc ctggcagcta aaaggaacg caagaaagga aaagaccctc atcagttcac         420
tgaacccttt aatgtctcct gtccaacag tgaggagtta catgaaacgg acaagttgtc        480
tgaaactcca gatcctggac taccagatgc ttacacaacc tggttggggt ttgtgggccg       540
aactgatgat ggggcaaact ctaaaaagaa atgtaagggg aaggacaaga aactacgtgg       600
actgtttgga ccaccaggac caccgggacc ccaaggacca cctggtcctc aggaatgcc        660
```

-continued

| | |
|---|---|
| tggagctgag gttacatatg aagtcttgct acaggatttc aaacaaatgc tgaaagaggc | 720 |
| cacagagcgc cgcttgatgt caggtgacat cccagaacac accagcgagc tgcctcccat | 780 |
| tgtgttacct gttgaggacc tttctcctta ccgacgggta gatgaaggtt tccattgcag | 840 |
| actgaaggga caagtcattg tggacaagaa gactttggtc gagctccaga actttcaaat | 900 |
| gccaacagcg aagggtcat tcctaagagg atctggactg aatttagcga caggacgctt | 960 |
| cacagcttca gtccccggga tttaccaatt ctcagcccat gttcatattg atcacagtga | 1020 |
| gatcaagagt aaagcgcaat tgcgccctcg tgacaacgtg cgggtgttaa tatgcattga | 1080 |
| gtctatgtgc catcgatata cgtcgctgga agtcattgct ggtttggaaa gcaacagtaa | 1140 |
| gatattcact gttcacgtgc aagggttgtt acagttgcag gttggccaat acacctctat | 1200 |
| atttgtggac aacagtgctg gagctccaat cactgtacaa aatgggtctg attttatggg | 1260 |
| cattcttatg ggtcttaag caaaccccga gaactgcaga aagcttctct ttgactccaa | 1320 |
| accagcgaca ttccgactaa cacattcaga cacctgcaaa gaataacaat ttcatgtggt | 1380 |
| ccagtcaaga tctgctccag attatatgct tggcaattac agcatgaggg acagaaatga | 1440 |
| tgtaggactt ttccctgct gctgctgctt atagaccttc tacatccaga gaaaacatat | 1500 |
| ttcaaagata atgctttgca agttccttta ccagtgaagg agttaatata tatcttctgg | 1560 |
| acactgtaaa aatatagttt taagtagagg aacccgcccc cctttttatt tgttgctatc | 1620 |
| ggttgagtcc tggactagga tggagagctc aaaaagtgct tttatttaa gactatgctg | 1680 |
| actctgtgct gaatcaacta ctacggacat ggtttttaag gggaactttt cggtgtggtt | 1740 |
| cctggattga tcagtaagga actgaagaaa agaatggtt gttcttgtga cactattatt | 1800 |
| ccacagattg ttaactcttc gaagcattga gccctgtatt gttttatat tataaagtgc | 1860 |
| tgcatacaat ggctgtatgt taataaacag tactttcaca ttaaaaaaaa aaaaaaaaa | 1919 |

<210> SEQ ID NO 12
<211> LENGTH: 1528
<212> TYPE: DNA
<213> ORGANISM: Danio rerio

<400> SEQUENCE: 12

| | |
|---|---|
| gactgtgata gagtctgctt tctgacccaa caacggtctc ctggctggtg ggctgaagat | 60 |
| gcgttgctgg gtactagctg tggtgacggc tgtgctctgg agccagtgca tccctctagg | 120 |
| gtgggccgag ggcaggaagg tgcctaagag gctgaaggaa ggcgctccac agcacaccga | 180 |
| agcattcaac accactcttt ccaacagcga ggagctggat ggcagcccaa agcaggttgg | 240 |
| tgagaatcag agagtggacc ctcttgggtc atggatggac tttgtgaaga gacctgtggg | 300 |
| caactttcct ggaaaatgca gaaacggaa acgaccactg cctggtcccc caggccctcc | 360 |
| aggtcctcca gggcctcagg gaccccagg agccccggg gcagaggtca ctcaggaggt | 420 |
| cctgctgcga gagttcaaag aaatgatcaa agaggccacg gagaggagag cagcagtgga | 480 |
| ccggcccagt gaacctagtc agctgcccac ggctctgatt acactggagg gcatgacctc | 540 |
| ctacaggaga atcgaggaag cgttccattg caaactcaaa ggccctgtgg tcgtggacaa | 600 |
| aaagactctg gcagagctgc agaactttca gacacctcct gccaaaggtg ccttcctcag | 660 |
| agggacgggg atggatcagt ccactggccg atttacagct cctgtaactg gaatttatca | 720 |
| gttctctgcc aatgttcata ttgaccacac tgaggtgaag agaagtaaga gccagctgag | 780 |
| agccagagac aacgtccgag ttttgatctg catcgaatcg ctctgtcaca gatatacatc | 840 |
| cttggaaatg attgttggcc ttgagagtaa cagcaagata ttcacagtat ctgttcatgg | 900 |

```
actgctggaa cttcaggctg gccagtacac ctctatattt gtggacaatg cagctggagc    960
gtcgatcaca atacagaacg gttccgattt catgggcatg ttgttgggtg tatagccgtg   1020
ttttacagcc agagactgta tatctggcgg gccacgtaag actgcacagc tcctcttcgg   1080
acaatcaaca agcaccataa atcctcatga acaatatct gaccgccaca aagcttttgg    1140 cttgttttg gaagagacac agacacatta aacccacaca gcagagacag ttggacacga    1200
aactgaaaga ctttaatgag gacagtagat ctgcctttct catgcgccgt gaggttgtta   1260
cctcatcaga aagatctttt tttaaaatat caagtctgat tttgttatat atagatgtat   1320
acgaagagat ttttgtactt tgatgtgttg ttatgtatgt cttttttttcc tcttaattaa   1380 tagtttatat acagagtgtt tatttacaca atttatttta tacggtgaga ggttttctac   1440
aatacaggag attatctttt ggatttatct taaagggaaa gttcacccaa aaaaaaaaa    1500 gaaaaaaaaa aaaaaaaaaa aaaaaaa                                       1528
```

```
<210> SEQ ID NO 13
<211> LENGTH: 4
<212> TYPE: PRT
<213> ORGANISM: Mus Musculus

<400> SEQUENCE: 13

Lys Lys Ser Arg
1

<210> SEQ ID NO 14
<211> LENGTH: 4
<212> TYPE: PRT
<213> ORGANISM: Homo sapiens

<400> SEQUENCE: 14

Lys Lys Pro Arg
1

<210> SEQ ID NO 15
<211> LENGTH: 4
<212> TYPE: PRT
<213> ORGANISM: Equua caballas

<400> SEQUENCE: 15

Lys Lys Leu Arg
1

<210> SEQ ID NO 16
<211> LENGTH: 4
<212> TYPE: PRT
<213> ORGANISM: Danio rerio

<400> SEQUENCE: 16

Pro Leu Pro Gly
1

<210> SEQ ID NO 17
<211> LENGTH: 25
<212> TYPE: DNA
<213> ORGANISM: Mus musculus

<400> SEQUENCE: 17
cggagactga gccatgtggg cctgg                                          25
```

<210> SEQ ID NO 18
<211> LENGTH: 25
<212> TYPE: DNA
<213> ORGANISM: Mus musculus

<400> SEQUENCE: 18
cgtttcttca gctccgctag gtacc                                          25

<210> SEQ ID NO 19
<211> LENGTH: 20
<212> TYPE: DNA
<213> ORGANISM: Artificial Sequence
<220> FEATURE:
<223> OTHER INFORMATION: synthetic sequence

<400> SEQUENCE: 19
cgattcacag ccccagtctc                                                20

<210> SEQ ID NO 20
<211> LENGTH: 19
<212> TYPE: DNA
<213> ORGANISM: Artificial Sequence
<220> FEATURE:
<223> OTHER INFORMATION: synthetic sequence

<400> SEQUENCE: 20
gtgcaggctg gcagaaaac                                                 19

<210> SEQ ID NO 21
<211> LENGTH: 21
<212> TYPE: DNA
<213> ORGANISM: Artificial sequence
<220> FEATURE:
<223> OTHER INFORMATION: synthetic sequence

<400> SEQUENCE: 21
cgactcgcta tctccaagtg a                                              21

<210> SEQ ID NO 22
<211> LENGTH: 20
<212> TYPE: DNA
<213> ORGANISM: Artificial Sequence
<220> FEATURE:
<223> OTHER INFORMATION: synthetic sequence

<400> SEQUENCE: 22
gttgaaccag tctccgacca                                                20

<210> SEQ ID NO 23
<211> LENGTH: 21
<212> TYPE: DNA
<213> ORGANISM: Artificial Sequence
<220> FEATURE:
<223> OTHER INFORMATION: synthetic sequence

<400> SEQUENCE: 23
ctgcataacg gtctggactt c                                              21

<210> SEQ ID NO 24
<211> LENGTH: 19
<212> TYPE: DNA
<213> ORGANISM: Artificial Sequence
<220> FEATURE:
<223> OTHER INFORMATION: synthetic sequence

```
<400> SEQUENCE: 24
cagcaactgc ccgtactcc                                              19

<210> SEQ ID NO 25
<211> LENGTH: 20
<212> TYPE: DNA
<213> ORGANISM: Artificial Sequence
<220> FEATURE:
<223> OTHER INFORMATION: synthetic sequence

<400> SEQUENCE: 25
gtggctgtgg agaagctgtg                                             20

<210> SEQ ID NO 26
<211> LENGTH: 21
<212> TYPE: DNA
<213> ORGANISM: Artificial Sequence
<220> FEATURE:
<223> OTHER INFORMATION: synthetic sequence

<400> SEQUENCE: 26
gaaggtccac gggaaagaca c                                           21

<210> SEQ ID NO 27
<211> LENGTH: 21
<212> TYPE: DNA
<213> ORGANISM: Artificial Sequence
<220> FEATURE:
<223> OTHER INFORMATION: synthetic sequence

<400> SEQUENCE: 27
ttccatccag ttgccttctt g                                           21

<210> SEQ ID NO 28
<211> LENGTH: 19
<212> TYPE: DNA
<213> ORGANISM: Artificial Sequence
<220> FEATURE:
<223> OTHER INFORMATION: synthetic sequence

<400> SEQUENCE: 28
gaaggccgtg gttgtcacc                                              19

<210> SEQ ID NO 29
<211> LENGTH: 20
<212> TYPE: DNA
<213> ORGANISM: Artificial Sequence
<220> FEATURE:
<223> OTHER INFORMATION: synthetic sequence

<400> SEQUENCE: 29
atgctgggac agtgacctgg                                             20

<210> SEQ ID NO 30
<211> LENGTH: 20
<212> TYPE: DNA
<213> ORGANISM: Artificial Sequence
<220> FEATURE:
<223> OTHER INFORMATION: synthetic sequence

<400> SEQUENCE: 30
ccttgatggt ggtgcatgag                                             20
```

```
<210> SEQ ID NO 31
<211> LENGTH: 23
<212> TYPE: DNA
<213> ORGANISM: Artificial Sequence
<220> FEATURE:
<223> OTHER INFORMATION: synthetic sequence

<400> SEQUENCE: 31
ttaaaaacct ggatcggaac caa                                              23

<210> SEQ ID NO 32
<211> LENGTH: 23
<212> TYPE: DNA
<213> ORGANISM: Artificial Sequence
<220> FEATURE:
<223> OTHER INFORMATION: synthetic sequence

<400> SEQUENCE: 32
gcattagctt cagatttacg ggt                                              23

<210> SEQ ID NO 33
<211> LENGTH: 23
<212> TYPE: DNA
<213> ORGANISM: Artificial Sequence
<220> FEATURE:
<223> OTHER INFORMATION: synthetic sequence

<400> SEQUENCE: 33
ttctctgtac catgacactc tgc                                              23

<210> SEQ ID NO 34
<211> LENGTH: 21
<212> TYPE: DNA
<213> ORGANISM: Artificial Sequence
<220> FEATURE:
<223> OTHER INFORMATION: synthetic sequence

<400> SEQUENCE: 34
cgtggaatct tccggctgta g                                                21

<210> SEQ ID NO 35
<211> LENGTH: 20
<212> TYPE: DNA
<213> ORGANISM: Artificial Sequence
<220> FEATURE:
<223> OTHER INFORMATION: synthetic sequence

<400> SEQUENCE: 35
gcaattattc cccatgaacg                                                  20

<210> SEQ ID NO 36
<211> LENGTH: 20
<212> TYPE: DNA
<213> ORGANISM: Artificial Sequence
<220> FEATURE:
<223> OTHER INFORMATION: synthetic sequence

<400> SEQUENCE: 36
ggcctcacta aaccatccaa                                                  20

<210> SEQ ID NO 37
<211> LENGTH: 33
<212> TYPE: DNA
<213> ORGANISM: Artificial Sequence
<220> FEATURE:
<223> OTHER INFORMATION: synthetic sequence
```

<400> SEQUENCE: 37
cgtgtggatt cccccgctat taccacgtcc aac					33

<210> SEQ ID NO 38
<211> LENGTH: 33
<212> TYPE: DNA
<213> ORGANISM: Artificial Sequence
<220> FEATURE:
<223> OTHER INFORMATION: synthetic sequence

<400> SEQUENCE: 38
gttggacgtg gtaatagcgg gggaatccac acg					33

<210> SEQ ID NO 39
<211> LENGTH: 34
<212> TYPE: DNA
<213> ORGANISM: Artificial Sequence
<220> FEATURE:
<223> OTHER INFORMATION: synthetic sequence

<400> SEQUENCE: 39
gtcctctaga aaacgggctc gtggccggga caag					34

<210> SEQ ID NO 40
<211> LENGTH: 34
<212> TYPE: DNA
<213> ORGANISM: Artificial Sequence
<220> FEATURE:
<223> OTHER INFORMATION: synthetic sequence

<400> SEQUENCE: 40
cttgtcccgg ccacgagccc gttttctaga ggac					34

<210> SEQ ID NO 41
<211> LENGTH: 34
<212> TYPE: DNA
<213> ORGANISM: Artificial Sequence
<220> FEATURE:
<223> OTHER INFORMATION: synthetic sequence

<400> SEQUENCE: 41
ccgggacaag aagtcggcag gcctctcagg tctc					34

<210> SEQ ID NO 42
<211> LENGTH: 34
<212> TYPE: DNA
<213> ORGANISM: Artificial Sequence
<220> FEATURE:
<223> OTHER INFORMATION: synthetic sequence

<400> SEQUENCE: 42
gagacctgag aggcctgccg acttcttgtc ccgg					34

<210> SEQ ID NO 43
<211> LENGTH: 45
<212> TYPE: DNA
<213> ORGANISM: Artificial Sequence
<220> FEATURE:
<223> OTHER INFORMATION: synthetic sequence

<400> SEQUENCE: 43
cggtgtcgtg gccgggacgc ggcgtcggca ggcctctcag gtctc					45

```
<210> SEQ ID NO 44
<211> LENGTH: 45
<212> TYPE: DNA
<213> ORGANISM: Artificial Sequence
<220> FEATURE:
<223> OTHER INFORMATION: synthetic sequence

<400> SEQUENCE: 44
gagacctgag aggcctgccg acgccgcgtc ccggccacga caccg          45
```

METHOD OF TREATING DIABETES BY A CTRP12 POLYPEPTIDE

REFERENCE TO RELATED APPLICATIONS

This application is a 35 U.S.C. §371 U.S. national entry of International Application PCT/US2012/033015 having an international filing date of Apr. 11, 2012, which claims the benefit of U.S. Provisional Application No. 61/474,220 filed Apr. 11, 2011, the content of each of the aforementioned applications is herein incorporated by reference in their entirety.

INCORPORATION-BY-REFERENCE OF MATERIAL SUBMITTED ELECTRONICALLY

This application contains a sequence listing. It has been submitted electronically via EFS-Web as an ASCII text file entitled "P11446-02_ST25". The sequence listing is 32,888 bytes in size, and was created on Mar. 15, 2012. It is hereby incorporated by reference in its entirety.

STATEMENT OF GOVERNMENTAL INTEREST

This invention was made with government support under grant nos. DK084171, DK084607, and DK079637 awarded by the National Institutes of Health. The government has certain rights in the invention.

BACKGROUND OF THE INVENTION

The results of the National Health and Nutrition Examination Survey 2003-2004 indicate that an estimated two-thirds of U.S. adults are either overweight or obese, and the prevalence of obesity is increasing, especially in young people, affecting approximately 17% of Americans 2-19 years of age. With increased obesity, there is an elevation of lipids in the bloodstream, termed lipidemia, which is a major risk factor for the development of metabolic syndrome and heart disease, the number one causes of death in the U.S.

Type 2 diabetes mellitus (T2DM) and associated pathologies are a major public health concern in the United States and worldwide. Efforts to treat T2DM are hampered by our incomplete understanding of the complex metabolic pathways and inter-tissue crosstalk involved in the control of whole-body glucose and fatty acid metabolism. Many secreted endocrine factors/hormones play key roles in mediating inter-tissue crosstalk to maintain energy balance. In recent years, adipose tissue-secreted factors (collectively termed adipokine) have emerged as important "metabolic regulators" that act on multiple tissue types to modulate processes including food intake, insulin sensitivity, glucose and fatty acid utilization, and inflammation. The functions of these adipokines are important for normal metabolic homeostasis; dysregulation of the pathways they modulate contributes to metabolic diseases, such as obesity, inflammation, and T2DM.

Thus, a need exists for an effective treatment for complications associated with obesity, Type 2 diabetes, and metabolic syndrome, specifically by helping to control blood glucose levels, and specifically, a need exists to identify novel factors regulating inter-tissue crosstalk, such that methods for treating disorders such as Type 2 diabetes mellitus can be developed.

SUMMARY OF THE INVENTION

The present invention relates to the seminal discovery of an adipokine and peptide portion thereof that is effective in lowering blood glucose levels in obese animal models. Thus, in accordance with an embodiment, the present invention provides a pharmaceutical composition comprising an amino acid sequence having a globular C1q/TNF-like domain, in an amount effective to treat T2DM, and a pharmaceutically acceptable carrier.

In accordance with another embodiment, the present invention provides the aforementioned pharmaceutical composition, wherein the amino acid sequence is selected from the group consisting of a) C1q/TNF-related protein-12 (CTRP12); b) a functional fragment of a); c) a functional homolog of a) or b) or functional fragment thereof; and d) a fusion polypeptide comprising an amino acid sequence of any of a) to c).

In accordance with another embodiment, the present invention provides the aforementioned pharmaceutical composition, wherein the amino acid sequence has an activity selected from the group consisting of a) reduction of blood glucose level; b) improvement of insulin sensitivity; c) normalization of hyperglycemia; d) suppression of gluconeogenesis; e) promotion of glucose uptake; f) suppression of hepatic lipogenic program; g) activation of PI3K-Akt signaling pathway; and h) any combination of two or more of a) through g).

In accordance with a further embodiment, the present invention provides an isolated or substantially purified peptide portion of an adipokine polypeptide.

In accordance with an embodiment, the present invention provides a method for treating T2DM comprising administering to a subject a) an amino acid sequence selected from the group consisting of 1) CTRP12 (e.g., SEQ ID NO: 1 or SEQ ID NO: 2); 2) a functional fragment of 1); 3) a functional homolog of 1) or 2) or functional fragment thereof; and 4) a fusion polypeptide comprising an amino acid sequence of any of 1) to 3); b) a substantially purified nucleic acid molecule encoding a polypeptide of any of 1) to 4); c) a vector comprising a nucleic acid molecule according to b); d) a host cell transformed with the vector of c); e) a ligand that specifically binds to a polypeptide of any of 1) to 4); f) a compound that modifies the level of expression or activity of the amino acid sequence according to any of 1) to 4); g) a pharmaceutical composition comprising any one of a) to f), and a pharmaceutically acceptable carrier; and h) any combination of two or more of a) through g).

BRIEF DESCRIPTION OF THE DRAWINGS

FIG. 9 provides the sequence alignment of CTRP12 proteins from different species, where the mouse is SEQ ID NO: 1, human is SEQ ID NO: 2, horse is SEQ ID NO: 3, chicken is SEQ ID NO: 4, frog is SEQ ID NO: 5, an zebra fish is SEQ ID NO: 6. Identical residues are highlighted in black. Conserved substitutions are highlighted in gray.

FIG. 18 is an amino acid sequence alignment of mouse (SEQ ID NO: 2), human (SEQ ID NO: 1), chicken (SEQ ID NO: 4), xenopus (SEQ ID NO: 5), and zebrafish (SEQ ID NO: 6) CTRP12. Highlighted are the conserved Asn-39 shown to be glycosylated in this study, the cleavage motif 'KKXR', and the Cys-85 shown in this study to be important for disulfide-linked multimerization of CTRP12.

DETAILED DESCRIPTION OF THE INVENTION

Figure 1:
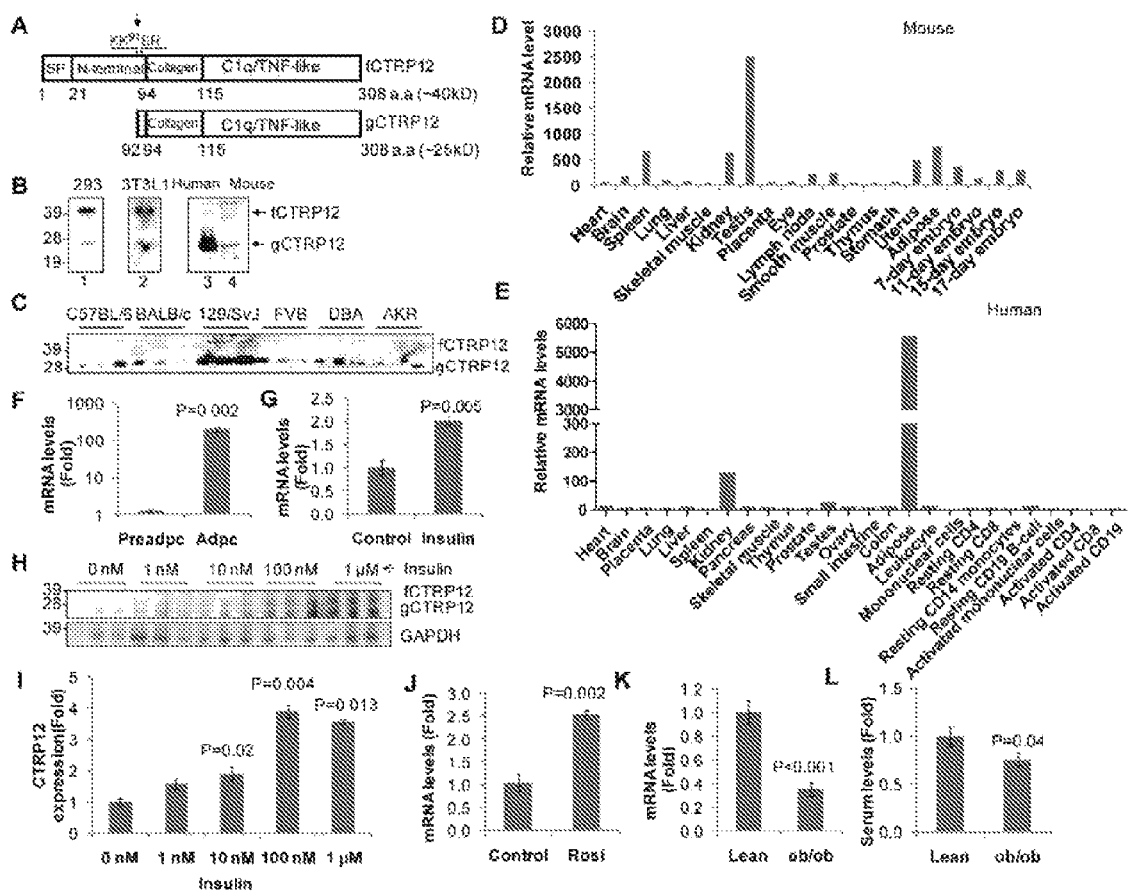
FIG. 1 shows that CTRP12 is a novel adipokine regulated by insulin. (A) The predicted modular components of full-length and globular CTRP12. Full-length CTRP12 comprises four domains: a signal peptide (SP), an N-terminal region, a collagen domain with 8 Gly-X-Y repeats, and a C1q/TNF-like domain. The cleavage site is indicated by the arrow. fCTRP12, full-length CTRP12. gCTRP12, globular CTRP12. (B) Immunoblot analysis of CTRP12 secreted into the medium of transfected HEK 293 cells (lane 1), endogenous CTRP12 secreted into the medium of 3T3-L1 adipocytes (lane 2), and CTRP12 present in human (lane 3) and mouse (lane 4) sera. (C) Immunoblot analysis of serum CTRP12 from different mouse strains showing that the cleaved CTRP12 (gCTRP12) is the major circulating form. (D-E) The expression profiles of CTRP12 mRNA in mouse (D) and human (E) tissues by quantitative real-time PCR analysis. (F) The expression of CTRP12 mRNA in pre-adipocytes and adipocytes (n=3). (G-I) The expression of CTRP12 mRNA in 3T3-L1 adipocytes is increased by insulin (10 nM, 24-hr incubation; n=6) (G), and the amount of CTRP12 protein is also increased by insulin in a dose-dependent manner (cell lysate, 24-hr incubation, n=3) (H-I). (J) The expression of CTRP12 mRNA is increased by rosiglitazone (1 µM for 6 hr; n=6). (K-L) CTRP12 mRNA levels in epididymal fat pad (n=6) (K) and serum CTRP12 levels (L) are decreased in ob/ob mice (male, 12-wk-old, n=8) compared to age-matched lean controls. All values in quantitative real-time PCR analysis (D-G, J-K) were normalized against 18S rRNA levels in each sample. All data are expressed as mean±SEM.

Despite the prevalence of insulin resistance and Type 2 diabetes mellitus (T2DM), their underlying mechanisms remain incompletely understood. Many secreted endocrine factors and the inter-tissue crosstalk they mediate are known to be dysregulated in T2DM.

In accordance with an embodiment, the present invention provides C1q/TNF-related protein-12 (CTRP12), a novel adipokine with antidiabetic actions. The mRNA and circulating levels of CTRP12 were decreased in a mouse model of obesity, but its expression in adipocytes was increased by the anti-diabetic drug rosiglitazone.

A modest rise in circulating levels of CTRP12 by recombinant protein administration is sufficient to lower blood glucose in wild-type, leptin-deficient ob/ob, and diet-induced obese (DIO) nice. A short-term elevation of serum CTRP12 in obese and diabetic mice by adenovirus-mediated expression improved insulin sensitivity and normalized hyperglycemia and hyperinsulinemia. Enhancement of insulin sensitivity is correlated with a decrease in serum levels of resistin, an adipokine known to induce insulin resistance. In hepatocytes and adipocytes, CTRP12 activated the PI3K-Akt signaling pathway to suppress gluconeogenesis and promote glucose uptake, respectively. Expression of CTRP12 also suppressed the hepatic lipogenic program in obese and diabetic mice. These data establish CTRP12 as a novel metabolic regulator linking adipose tissue to whole-body glucose and lipid homeostasis.

All CTRPs are secreted multimeric proteins, produced by diverse tissues, and the majority are found circulating in plasma, with levels varying depending on metabolic state and genetic background. The defining feature of CTRPs is the presence of the signature "C1q/TNF-like" globular domain located at the C-terminus, which is homologous to the immune complement C1q and structurally resembles that of TNF-α. Functional studies thus far have indicated significant roles for CTRPs in the endocrine, immune, vascular, skeletal, and visual systems.

In the present study, the function and mechanisms of action of CTRP12, a novel and distantly related member of the CTRP family were characterized. Using recombinant protein administration and adenovirus-mediated expression, evidence is provided that CTRP12 is a novel adipokine with anti-diabetic actions in both genetic (leptin-deficient) and diet-induced mouse models of obesity and diabetes. CTRP12 ameliorates insulin resistance in part by activating the PI3K-Akt signaling pathway, independent of insulin, to suppress gluconeogenesis in hepatocytes and promote glucose uptake in adipocytes. Based on in vivo anti-diabetic actions, that circulating levels are decreased in obesity, and expression in adipocytes is increased by the anti-diabetic drug rosiglitazone, CTRP12 is a potential therapeutic agent and target in the treatment of T2DM.

The term, "Type 2 diabetes mellitus" refers to Type 2 diabetes mellitus and related disorders such as obesity, hyperglycemia, and hyperinsulinemia. Subjects suffering from Type 2 diabetes mellitus can be treated according to the present invention by administration of CTRP12, which enhances insulin sensitivity and promotes glucose uptake by cells. Other diseases characterized by insulin dysfunction or insufficient glucose transport into cells can be treated according to the present invention by administration of CTRP12 which enhances insulin sensitivity and promotes glucose uptake by cells.

The term, "amino acid" includes the residues of the natural α-amino acids (e.g., Ala, Arg, Asn, Asp, Cys, Glu, Gln, Gly, His, Hyl, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," as used herein, includes a sequence of from four to sixteen amino acid residues in which the α-carboxyl group of one amino acid is joined by an amide bond to the main chain (α- or β-) amino group of the adjacent amino acid. The peptides provided herein for use in the described and claimed methods and compositions can be cyclic.

The term, "amount effective to treat Type 2 diabetes mellitus" is that amount effective to treat, ameliorate, or prevent Type 2 diabetes mellitus or symptoms thereof, or to exhibit a detectable therapeutic or preventative effect.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

In one embodiment, the carrier is a pharmaceutically acceptable carrier. With respect to pharmaceutical compositions, the carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), and one which has little or no detrimental side effects or toxicity under the conditions of use.

The choice of carrier will be determined in part by the particular CTRP12, as well as by the particular method used to administer the CTRP12 material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive CTRP12, and in certain instances, a particular route can provide a more immediate and more effective response than another route.

Topical formulations are well-known to those of skill in the art. Such formulations are particularly suitable in the context of the invention for application to the skin.

The CTRP12, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

The carriers or diluents used herein may be solid carriers or diluents for solid formulations, liquid carriers or diluents for liquid formulations, or mixtures thereof.

Solid carriers or diluents include, but are not limited to, gums, starches (e.g. corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include sodium chloride solution, Ringer's dextrose, dextrose and sodium chloride, lactated Ringer's and fixed oils. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The parenteral formulations will typically contain from about 0.5% to about 25% by weight of CTRP12 material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

It will be appreciated by one of skill in the art that, in addition to the above-described pharmaceutical compositions, the CTRP12 of the invention can be formulated as inclusion complexes, such as cyclodextrin inclusion complexes, or liposomes.

Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compositions comprising CTRP12 or derivatives thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

Therapeutic compositions generally are placed into a container having a sterile access port, for example, an intravenous solution bag or vial having a stopper pierceable by a hypodermic injection needle. The route of administration of CTRP12, or a derivative thereof, in accordance with the present invention, is in accord with known methods, e.g., injection or infusion by intravenous, intraperitoneal, intramuscular, intraarterial, subcutaneous, intralesional routes, by aerosol or intranasal routes, or by sustained release systems as noted below. CTRP12 or its derivatives can be administered continuously by infusion or by bolus injection.

The choice of carrier will be determined, in part, by the chemical characteristics of CTRP12 or derivatives thereof, as well as by the particular method used to administer it. Accordingly, there are a variety of suitable formulations of the pharmaceutical composition of the invention. The following formulations for parenteral, subcutaneous, intravenous, intramuscular, intraarterial, intrathecal, and interperitoneal administration are exemplary and are in no way limiting. More than one route can be used to administer CTRP12 or derivatives thereof, and in certain instances, a particular route can provide a more immediate and more effective response than another route.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of CTRP12 or derivatives thereof, administered should be sufficient to effect, e.g., a therapeutic or prophylactic response, in the subject over a reasonable time frame. The dose will be determined by the efficacy of CTRP12 or derivatives thereof, and the condition of a subject, as well as the body weight of a subject to be treated.

An effective amount of CTRP12 or derivatives thereof, to be employed therapeutically will depend, for example, upon the therapeutic and treatment objectives, the route of administration, the age, condition, and body mass of the subject undergoing treatment or therapy, and auxiliary or adjuvant therapies being provided to the subject. Accordingly, it will be necessary and routine for the practitioner to titer the dosage and modify the route of administration, as required, to obtain the optimal therapeutic effect. A typical daily dosage might range from about 0.1 mg/kg to up to about 100 mg/kg or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays.

Alternatively, the CTRP12 or derivatives thereof can be modified into a depot form, such that the manner in which the inventive TCR materials is released into the body to which it is administered is controlled with respect to time and location within the body (see, for example, U.S. Pat. No. 4,450,150). Depot forms of CTRP12 or derivatives thereof can be, for example, an implantable composition comprising the CTRP12 or derivatives thereof and a porous or non-porous material, such as a polymer, wherein the CTRP12 or derivatives thereof is encapsulated by or diffused throughout the material and/or degradation of the non-porous material. The depot is then implanted into the desired location within the body and the CTRP12 or derivatives thereof are released from the implant at a predetermined rate.

The dosage ranges for the administration of CTRP12 or derivatives thereof, are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication.

Generally, when CTRP12 or derivatives thereof, are administered together with additional therapeutic agents, lower dosages can be used. CTRP12 or derivatives thereof, can be administered parenterally by injection or by gradual perfusion over time. CTRP12 or derivatives thereof, can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The present invention includes methods of use of full length CTRP12 proteins as well as functional fragments thereof (e.g., amino acids 92-308 of SEQ ID NO: 2; 98-302 of SEQ ID NO: 1, or functional equivalents thereof in other species, including human).

In accordance with an embodiment, the present invention provides a method for treating T2DM comprising administering to a subject a) an amino acid sequence selected from the group consisting of 1) CTRP12 (e.g., SEQ ID NO: 1 or SEQ ID NO: 2); 2) a functional fragment of 1); 3) a functional homolog of 1) or 2) or functional fragment thereof; and 4) a fusion polypeptide comprising an amino acid sequence of any of 1) to 3); b) a substantially purified nucleic acid molecule encoding a polypeptide of any of 1) to 4); c) a vector comprising a nucleic acid molecule according to b); d) a host cell transformed with the vector of c); e) a ligand that specifically binds to a polypeptide of any of 1) to 4); f) a compound that modifies the level of expression or activity of the amino acid sequence according to any of 1) to 4); g) a pharmaceutical composition comprising any one of a) to f), and a pharmaceutically acceptable carrier; and h) any combination of two or more of a) through g).

In accordance with another embodiment, the present invention provides a full length CTRP12 mutant protein, which retains the function of the wild type protein, but is not cleavable by intracellular endopeptidases.

In accordance with an embodiment, the above method of the present invention is exemplified by a functional fragment of CTRP12, being amino acids 92-308 of SEQ ID NO: 2.

With respect to the functional fragments of CTRP12, the functional portion can be any portion comprising contiguous amino acids of the CTRP12 of which it is a part, and is any part or fragment of CTRP12, which part or fragment retains the biological activity of the CTRP12 of which it is a part. Functional portions encompass, for example, those parts of a CTRP12 that retain the ability to a) reduction of blood glucose level; b) improvement of insulin sensitivity; c) normalization of hyperglycemia; d) suppression of gluconeogenesis; e) promotion of glucose uptake; f) suppression of hepatic lipogenic program; g) activation of PI3K-Akt signaling pathway; and h) any combination of one or more of a) through g), to a similar extent, the same extent, or to a higher extent, as the parent CTRP12. In reference to the parent CTRP12, the functional portion can comprise, for instance, about 10%, 25%, 30%, 50%, 68%, 80%, 90%, 95%, or more, of the parent CTRP12.

In accordance with another embodiment, the methods of treatment described above can further comprise administering to the subject one or more biologically active agents.

The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs. Preferred biologically active agents would include anti-lipid agents, anti-obesity agents, hyperglycemic agents, hypoglycemic agents, and anti-diabetic agents such as, for example, alpha-glucosidase inhibitors (starch inhibitors), sulfonylureas, biguanides, thizoladinediones, and insulin secretagogues. Examples of such anti-diabetic agents are arcarbose, miglitol, glimepiride, tolbutamide, metformin, piglitazone, rosiglitazone, and repaglinide.

The functional portion of the CTRP12 can comprise additional amino acids at the amino or carboxy terminus of the portion, or at both termini, which additional amino acids are not found in the amino acid sequence of the parent CTRP12. Desirably, the additional amino acids do not interfere with the biological function of the functional portion.

The invention further provides an isolated or purified protein comprising at least one of the polypeptides described herein. By "protein" is meant a molecule comprising one or more polypeptide chains.

In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof.

Included in the scope of the invention are functional variants of the inventive TCRs, polypeptides, and proteins described herein. The term "functional variant" as used herein refers to CTRP12, polypeptide, or protein having substantial or significant sequence identity or similarity to CTRP12, polypeptide, or protein, which functional variant retains the biological activity of CTRP12, polypeptide, or protein of which it is a variant. In reference to the parent CTRP12, polypeptide, or protein, the functional variant can, for instance, be at least about 30%, 50%, 75%, 80%, 90%, 98% or more identical in amino acid sequence to the parent CTRP12, polypeptide, or protein.

The functional variant can, for example, comprise the amino acid sequence of the parent CTRP12, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent CTRP12, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent CTRP12, polypeptide, or protein.

The CTRP12, polypeptide, or protein can consist essentially of the specified amino acid sequence or sequences described herein, such that other components of the functional variant, e.g., other amino acids, do not materially change the biological activity of the functional variant.

CTRP12, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

CTRP12, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When CTRP12, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

CTRP12, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CTRP12s, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, CTRP12, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive CTRP12, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

In accordance with another embodiment, the above method of the present invention is also exemplified by the amino acid sequence being a proteolytic fragment of an adipokine polypeptide, or a functional peptide portion thereof, said proteolytic fragment or functional peptide portion thereof having an activity selected from the group consisting of a) reduction of blood glucose level; b) improvement of insulin sensitivity; c) normalization of hyperglycemia; d) suppression of gluconeogenesis; e) promotion of glucose uptake; f) suppression of hepatic lipogenic program; g) activation of PI3K-Akt signaling pathway; and h) any combination of two or more of a) through g).

In accordance with a further embodiment, the above method of the present invention is also exemplified by the amino acid sequence being produced by cleavage of an adipokine polypeptide at a proteolytic cleavage site motif comprising the amino acid sequence: Lys-Lys-Ser-Arg (SEQ ID NO: 13).

In accordance with still another embodiment, the above method of the present invention is exemplified by said proteolytic cleavage site motif comprising an amino acid sequence corresponding to amino acid residues 90 to 93 as set forth in SEQ ID NO: 2.

In accordance with an embodiment, the present invention provides a pharmaceutical composition, as described above, wherein the functional fragment of CTRP12 is an amino acids sequence selected from about 92-308 as set forth in SEQ ID NO:2; and a functional peptide portion thereof.

Figure 9:
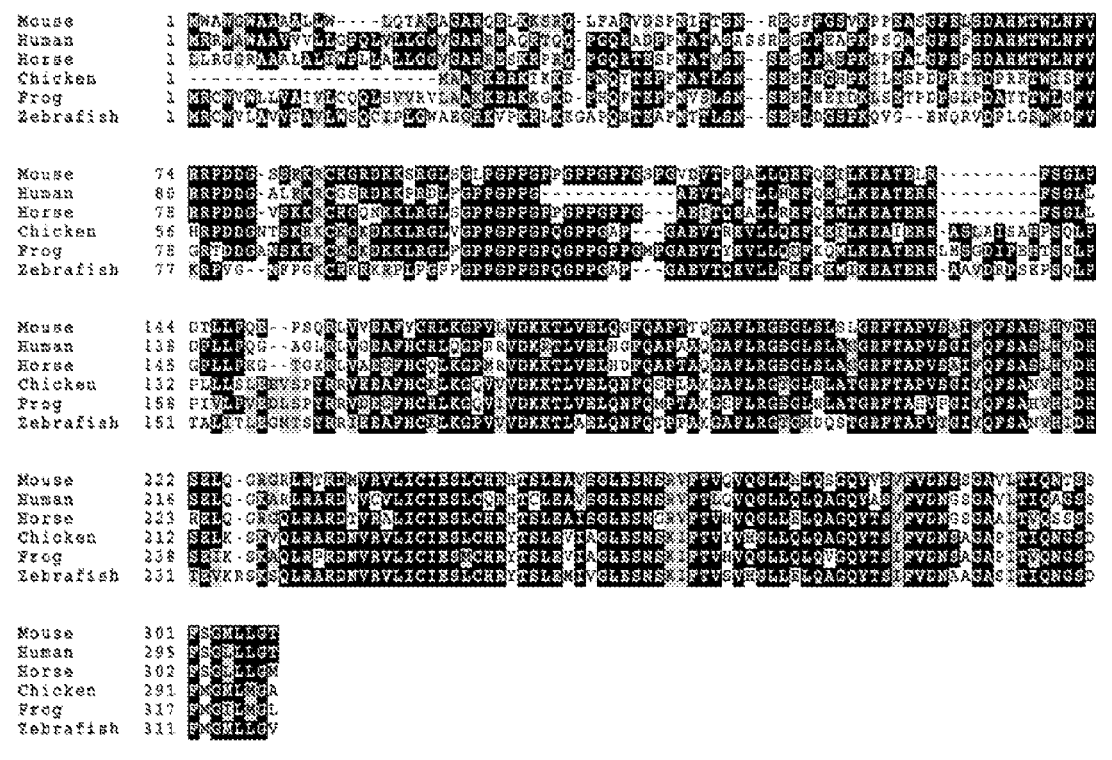

Alignment of the amino acid sequences of human, murine, chicken and other species as shown in FIG. 9 reveals that amino acid sequence homology in the C1q/TNF-like domain rCTRP12es from 67-83% homologous with human having 82% homology to the mouse sequence (92-308 of SEQ ID NO: 2) which has been identified as a biologically active fragment of CTRP12. Furthermore, the alignment shown in FIG. 9 demonstrates that CTRP12 and particularly the corresponding region from mouse of amino acid residues 92-308 are highly conserved among quite diverse species.

Polynucleotides encoding full length CTRP12 or biologically active C-terminal fragments are included herein. Further, the invention provides CTRP12 polynucleotide sequences encoding a CTRP12 polypeptide or C-terminal biologically active fragment thereof as described herein of at least about 60%, 65%, 70%, 75%, 80%, 85%, 90% or 95% identical to murine CTRP12 or C-terminal fragment 92-308 thereof (e.g., 98-302 of SEQ ID NO: 1, human).

In accordance with an embodiment, the present invention provides a polypeptide comprising the amino acid sequence of SEQ ID NO: 1, wherein about one to about 10 amino acids are mutated such that endopeptidase cleavage at amino acid Lys-91, cannot occur.

In accordance with another embodiment, the present invention provides a polypeptide comprising the amino acid sequence of SEQ ID NO: 1, wherein about one to about 10 amino acids mutated are located within 10 amino acids of the Lys-91 on the polypeptide. In yet another embodiment, the present invention provides a polypeptide comprising the amino acid sequence of SEQ ID NO: 1, wherein the polypeptide has the following mutated amino acids: K90A, K91A, and R93A.

In accordance with an embodiment, the present invention provides an adipokine polypeptide which is exemplified by a mammalian adipokine having an amino acid sequence such as that of human adipokine (SEQ ID NO: 1); mouse adipokine (SEQ ID NO: 2); horse adipokine (SEQ ID NO: 3); avian adipokine having an amino acid sequence such as that of chicken adipokine (SEQ ID NO: 4); by an amphibian adipokine having an amino acid sequence such as that of a frog adipokine (SEQ ID NO: 5); and by a piscine adipokine having an amino acid sequence such as that of a zebra fish adipokine (SEQ ID NO: 6).

A polynucleotide of the present invention can be as set forth above, or can be a polynucleotide complementary thereto, and can be a nucleotide sequence of at least 15 nucleotides, wherein the sequence specifically hybridizes a polynucleotide as set forth above.

The C-terminal polypeptide, may include the putative proteolytic processing site of CTRP12 (i.e., amino acid residues 90-93 of murine CTRP12, SEQ ID NO: 2). Mouse CTRP12 includes 90-KKSR-93 (SEQ ID NO: 13); human includes KKPR (SEQ ID NO: 14); horse, chicken and frog include KKLR (SEQ ID NO: 15); and Zebrafish PLPG (SEQ ID NO: 16).

In accordance with an embodiment, the present invention also provides a substantially purified peptide portion of an adipokine polypeptide, wherein the peptide is produced by cleavage of the adipokine polypeptide at a proteolytic cleavage site motif comprising the amino acid sequence: Lys-Lys-Ser-Arg (KKSR) (SEQ ID NO: 13). Such proteolytic cleavage site motif is exemplified by an amino acid sequence corresponding to amino acid residues 90 to 93 as set forth in SEQ ID NO: 2.

In accordance with an embodiment, the present invention further provides an isolated or purified nucleic acid molecule encoding the any of the aforementioned peptides or polypeptides, or functional portions thereof. In another embodiment the polynucleotides of the present invention include, for example, the nucleotide sequences SEQ ID NO: 7, SEQ ID NO: 8, SEQ ID NO: 9, SEQ ID NO: 10, SEQ ID NO: 11, and SEQ ID NO: 12.

Minor modifications of the CTRP12 primary amino acid sequence can result in proteins which have substantially equivalent activity as compared to the exemplified CTRP12 polypeptides. Such modifications can be deliberate, such as modification introduced by a method such as site-directed mutagenesis, or can be spontaneous. All of the polypeptides produced by these modifications are encompassed within the present invention, provided polypeptide maintains a function of CTRP12, as disclosed herein. Deletion of one or more amino acids can also result in a modification of the structure of the resultant molecule without significantly altering its biological activity. This can lead to the development of a smaller active molecule which would have broader utility (e.g., aa 92-308 of SEQ ID NO: 2). For example, one can remove amino or carboxy terminal amino acids which are not required for the biological activity or other function of CTRP12 or fragment 92-308 exemplified herein).

In accordance with an embodiment, the present invention provides a pharmaceutical composition as described herein, suitable for use as a medicament, preferably for use in the treatment of T2DM in a subject suffering therefrom.

In accordance with another embodiment, the present invention provides a pharmaceutical composition as described herein, suitable for use as a medicament, preferably for use in the treatment of metabolic syndrome in a subject suffering therefrom.

In accordance with a further embodiment, the present invention provides a pharmaceutical composition as described herein, suitable for use as a medicament, preferably for use in increasing insulin sensitivity in a subject.

In accordance with an embodiment, the present invention provides a pharmaceutical composition as described herein, suitable for use as a medicament, preferably for use in decreasing insulin resistance in a subject.

In accordance with yet another embodiment, the present invention provides a pharmaceutical composition as described herein, suitable for use as a medicament, preferably for use in increasing glucose uptake in the cells of a subject.

In accordance with a further embodiment, the present invention provides a pharmaceutical composition as described herein, suitable for use as a medicament, preferably for use in modulating the concentration of blood glucose in a subject.

Further provided by the invention is a nucleic acid comprising a nucleotide sequence encoding the CTRP12, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides substituted nucleic acid sequences which encode any of the substituted CTRP12s, substituted polypeptides, substituted proteins, or substituted functional portions or functional variants thereof.

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The polynucleotide sequence encoding a CTRP12 polypeptide of the invention includes the exemplified sequences, as well as conservative variations of the exemplified polypeptide sequences. The term "conservative variation" as used herein refers to a replacement of an amino acid residue by another, biologically similar amino acid residue. Examples of conservative variations include the substitution of a hydrophobic residue such as isoleucine, valine, leucine or methionine for another, or the substitution of a polar residue for another, such as the substitution of arginine for lysine, glutamic for aspartic acid, or glutamine for asparagine, and the like. The term "conservative variation" also includes the use of a substituted amino acid in place of an unsubstituted parent amino acid, provided that an antibody that specifically interacts with the substituted polypeptide also is specifically immunoreactive with the unsubstituted polypeptide.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CTRP12s. It is generally appreciated that conditions can be rendered more stringent by the addition of increasing amounts of formamide.

A polynucleotide of the invention can be obtained by several methods. For example, the polynucleotide can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Polynucleotides encoding CTRP12 polypeptides, including the C-terminal active fragment described herein exemplified by murine 92-308 of various organisms can be identified using well known procedures and algorithms based on identity or homology to the disclosed sequences. Homology or identity is often measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. The terms "homology" and "identity," when used herein in the context of two or more nucleic acids or polypeptide sequences, refer to two or more sequences or subsequences that are the same or have a specified percentage of amino acid residues or of nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

In certain exemplary embodiments, vectors such as, for example, expression vectors, containing a nucleic acid encoding one or more CTRP12 polypeptides described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more CTRP12 polypeptides or fragments thereof described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more CTRP12 polypeptides is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences, e.g., adipose tissue). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., CTRP12).

In certain exemplary embodiments, nucleic acid molecules described herein can be inserted into vectors and used as gene therapy vectors. Gene therapy vectors can be delivered to a subject by, for example, intravenous injection, local administration (see, e.g., U.S. Pat. No. 5,328,470), or by stereotactic injection (see, e.g., Chen et al. (1994) Proc. Natl. Acad. Sci. U.S.A. 91:3054). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, adeno-associated virus vectors, and the like, the pharmaceutical preparation can include one or more cells which produce the gene delivery system (See Gardlik et al. (2005) Med. Sci. Mon. 11:110; Salmons and Gunsberg (1993) Hu. Gene Ther. 4:129; and WCTRP12 et al. (2005) J. Virol. 79:10999 for reviews of gene therapy vectors).

A vector can be introduced in vivo in a non-viral vector, e.g., by lipofection, with other transfection facilitating agents (peptides, polymers and the like), or as naked DNA. Synthetic cationic lipids can be used to prepare liposomes for in vivo transfection, with targeting in some instances (Felgner, et. al., 1987; Felgner and Ringold, 1989; see Mackey, et al., 1988; Ulmer et al., 1993). Useful lipid compounds and compositions for transfer of nucleic acids are described in WO 95/18863, WO 96/17823 and in U.S. Pat. No. 5,459,127. Other molecules are also useful for facilitating transfection of a nucleic acid in vivo, such as, e.g., a cationic oligopeptide (See, e.g., WO 95/21931), peptides derived from DNA binding proteins (See, e.g., WO 96/25508) a cationic polymer (See, e.g., WO 95/21931) and the like. A relatively low voltage, high efficiency in vivo DNA transfer technique, termed electrotransfer, has been described (See, e.g., WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (See, e.g., Canadian Patent Application No. 2,012, 311). Receptor-mediated DNA delivery approaches can also be used. U.S. Pat. Nos. 5,580,859 and 5,589,466 disclose delivery of exogenous DNA sequences, free of transfection facilitating agents, in a mammal.

Alternatively, a subject having type 2 diabetes can be administered an effective amount of CTRP12 protein, peptide fragment, or variant of the invention. Therapeutic methods comprising administering CTRP12, fragments thereof or CTRP12 agonists are within the scope of the present invention. The present invention also provides for pharmaceutical compositions comprising CTRP12 protein, peptide fragment, or derivative in a suitable pharmacological carrier. The CTRP12 protein, peptide fragment, or variant may be administered systemically or locally. Applicable to the methods taught herein, the CTRP12 protein can be optionally administered prior to, after, or preferably concomitantly with insulin.

EXAMPLES

Cloning. CTRP12 (also called C1qTNF12) was cloned based on three overlapping EST sequences, BY704358, BI693294, and CO044841, from a mouse testis cDNA pool (Clontech). Primers were designed to amplify the entire coding region of mouse CTRP12 from a mouse testis cDNA pool (Clontech). The forward and reverse primers used in the 33-cycle PCR reactions were 5'-CGGAGACTGAGCCATG TGGGCCTGG-3' (SEQ ID NO: 17) and 5'-CGTTTCT-TCAGCTCCG CTAGGTACC-3' (SEQ ID NO: 18), respectively. The PCR product was purified and cloned into pCRII TOPO vector (Invitrogen), and the entire cDNA insert was sequenced. The sequence data for CTRP12 (C1qTNF12) was deposited into the NCBI GenBank database and was assigned the accession number DQ002404.

Quantitative real time (RT)-PCR analysis. CTRP12 tissue expression analysis was performed using mouse and human tissue cDNA panels (Clontech). Otherwise, RNAs were isolated from tissues or cell lines using Trizol® and reverse transcribed using Superscript II RNase H-reverse Transcriptase (Invitrogen). CTRP12 expression was normalized against 18 S rRNA in each sample. Expression of gluconeogenic and lipogenic genes in H4IIE cells was performed after cells had been treated with vehicle or CTRP12 (10 µg/ml) for 24 hours. Expression of these genes was normalized against the β-actin level in each sample. Primers used in real-time PCR included the following: CTRP12 forward 5'-CGAT-TCACAGCC CCAGTCTC-3' (SEQ ID NO: 19) and reverse 5'-GTGCAGGCTGGC AGAAAAC-3' (SEQ ID NO: 20); G6 Pase forward 5'-CGACTCGCTA TCTCCAAGTGA-3' (SEQ ID NO: 21) and reverse 5'-GTTGAACCA GTCTC-CGACCA-3' (SEQ ID NO: 22); PEPCK forward 5'-CTGCAT AACGGTCTGGACTTC-3' (SEQ ID NO: 23) and reverse 5'-CAGC AACTGCCCGTACTCC-3' (SEQ ID NO: 24); IL-1β forward 5'-GTG GCTGTGGAGAAGCTGTG-3' (SEQ ID NO: 25) and reverse 5'-GA AGGTCCACGG-GAAAGACAC-3' (SEQ ID NO: 26); IL-6 forward 5'-TTC-CATCCAGTTGCCTTCTTG-3' (SEQ ID NO: 27) and reverse 5'-GAAGGCCGTGGTTGTCACC-3' (SEQ ID NO: 28); TNF-α forward 5'-ATGCTGGGACAGTGACCTGG-3' (SEQ ID NO: 29) and reverse 5'-CCTTGATGGTGGTGCAT-GAG-3' (SEQ ID NO: 30); MCP-1 forward 5'-TTAAAAAC-CTGGATCGGAA CCAA-3' (SEQ ID NO: 31) and reverse 5'-GCATTAGCTTCAGATT TACGGGT-3' (SEQ ID NO: 32); MIP-1α forward 5'-TTCTCTGTA CCATGA-CACTCTGC-3' (SEQ ID NO: 33) and reverse 5'-CGTGGA ATCTTCCGGCTGTAG-3' (SEQ ID NO: 34); 18S rRNA forward 5'-GCAATTATTCCCCATGAACG-3'(SEQ ID NO: 35) and reverse, 5'-GGCCTCACTAAACCATCCAA-3' (SEQ ID NO: 36).

Protein purification. Recombinant CTRP12 was produced and purified as described (*Biochem. J.* 416, 161-177 (2008)). Briefly, HEK 293T cells were transfected with pcDNA3.1, encoding a C-terminal FLAG-tagged CTRP12, using lipofectamine 2000 (Invitrogen). Supernatants (serum-free Opti-MEM) of cells were collected and subjected to affinity chromatography using ANTI-FLAG® M2 Affinity Gel (sigma) according to the manufacturer's protocol. Purified protein was dialyzed against 25 mM Hepes (pH 8.0) containing 135 mM NaCl, concentrated with a 10K cut-off Amicon Ultra centrifugal filter (Millipore). Protein concentration was determined using the Coomasie Plus Protein Assay (Thermo Scientific). Purity of the protein (>95%) was determined by SDS-PAGE analysis and Coomasie blue staining.

N-terminal sequencing of gCTRP12. Recombinant CTRP12 was electroblotted onto PVDF membrane. The band corresponding to gCTRP12 was excised. Sequencing was performed at the mass spectrometry facility at Johns Hopkins University School of Medicine.

Figure 18:
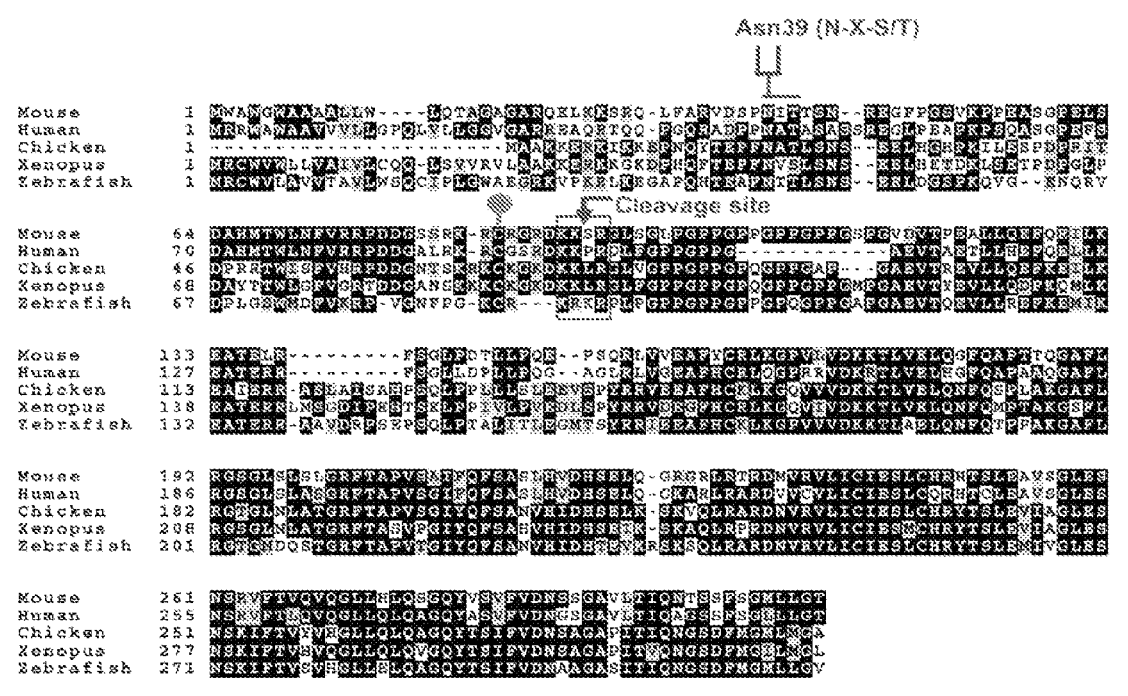

Generation of CTRP12-specific antibody. Rabbit anti-CTRP12 polyclonal antibody was produced as previously described (Id.). Anti-CTRP12 antibody specifically recognizes CTRP12, not other CTRPs (FIG. 18).

Mice. Male wild-type, ob/ob, and DIO mice (all on C57BL/6 background) were purchased from Jackson Laboratory. Mice were maintained on a standard chow diet with free access to food and water. Mice were housed in plastic cages on a 12 hour light-dark photocycle.

Streptozotocin administration. 7 weeks old male C57BL/6 mice were injected via IP with STZ (Sigma) dissolved in citrate buffer (50 mM, pH 4.5) at a dose of 200 mg/kg body weight.

Glucose uptake. 3T3-L1 cells were cultured and differentiated as described (*J Biol. Chem.* 285, 39691-39701 (2010). Glucose uptake in 3T3-L1 cells was performed as described (32). Cells were treated with vehicle or CTRP12 (10 µg/ml) for 30 minutes, and/or with insulin (10 nM) for 15 min, and/or with LY29004 for 1 hour.

Glucose production and measurement. This assay was performed as described in (*Assay Drug Dev Technol.* 4, 525-533 (2006)).

In vitro fatty acid oxidation. This assay was performed as described (*Proc Natl Acad Sci USA* 101, 10302-10307 (2004)) with the following chCTRP12es: H4IIE cells were treated with vehicle control or CTRP12 for 6 hours and were used for the assay.

In vivo fatty acid oxidation. This assay was performed as described (*Proc Natl Acad Sci USA* 102, 14557-14562 (2004)) with the following chCTRP12es: Mice were injected with [1 $^{14}$C] palmitatic acid at a dose of 1 µCi per mouse. $^{14}CO_2$ was collected at 20 minutes intervals for 1 hour.

Injection of recombinant CTRP12 into mice. Either vehicle control or CTRP12 was injected i.p. into C57BL/6 mice. Food was removed from the cage 3 hours before injection and during the course of the experiment. Tail vein blood glucose was measured by a glucometer (BD Pharmingen). Serum insulin, glucagon, and non-esterified fatty acid (NEFA) concentrations were measured using kits from Millipore (insulin and glucagon ELISA) and Wako (NEFA).

Insulin secretion assay. This assay was performed essentially as described (*Diabetes*, 49:424-430 (2000)), with the following chCTRP12es: Cells were seeded at a 0.1 million per well in 96-well plate and cultured until 100% confluence when the assay was performed. Insulin concentration was determined by the insulin ELISA kit (Millipore). Insulin concentration was normalized against the protein concentration of the cell lysate in each well.

Adenovirus preparation and infection. Adenovirus encoding GFP or CTRP12 was prepared using the AdEasy™ Adenoviral Vector System (Stratagene) according to the manufacturer's protocol. Either GFP- or CTRP12-encoding adenovirus was injected via tail vein into WT C56BL/6 male mice (9-wk-old) at the dose of $10^{11}$ viral particle per mouse. Adenoviruses were injected into ob/ob and DIO mice at the dose of $5 \times 10^{12}$ viral particles/kg body weight.

Glucose tolerance test (GTT). GFP- and CTRP12-expressing mice were fasted for 7 hr. Glucose was injected into mice via i.p. at a dose of 1 mg/g body weight. Blood glucose was measured using a glucometer (BD Pharmingen). Serum insulin and glucagon were measured using ELISA kit from Millipore.

Meal tolerance test (MTT). GFP- and CTRP12-expressing mice were overnight fasted. Blood glucose levels were measured and sera were obtained before mice were given unlimited access to food pellets for 1 hr. Blood glucose and sera were obtained again after 1 hour re-feeding. Food consumption during this 1 hour re-feeding was measured.

Blood chemistry analysis. Fasting metabolic parameters were obtained after a 7-hour fast. Overnight fasting parameters were obtained after 16-hour fast. Fed parameters were obtained in ad libitum fed mice with 2 hour food removal. Peptide and protein hormones were measured using corresponding ELISA or luminex kits from Millipore.

Site-directed Mutagenesis. High-fidelity Pfu polymerase from Stratagene was used in site-directed mutagenesis of CTRP12 cDNA to generate N39A, C85A, and R93A single-substitution proteins or the (K90A, K91A, R93A) triple-substitution proteins (designated as 3M) according to the manufacturer's protocol. Primers used in site-directed mutagenesis were as follows: N39A forward, 5'-CGTGTGGATTC-CCCCGCTATTACCACGTCCAAC-3' (SEQ ID NO: 37) and reverse, 5'-GTTGGAC GTGGTAATAGCGGGGGAATC-CACACG-3' (SEQ ID NO: 38); C85A forward, 5'-GTC-CTCTAGAAAACGGGCT CGTGGCCGGGACAAG-3' (SEQ ID NO: 39) and reverse, 5'-CTTGTCCCGGCCAC-GAGCCCGTTTTCTAGAG GAC-3' (SEQ ID NO: 40); R93A forward, 5'-CCGGGACA AGAAGTCGGCAGGC-CTCTCAGGTCTC-3' (SEQ ID NO: 41) and reverse, 5'-GAGACCTGAGAGGCCTGCCGACTT CTTGTC-CCGG-3' (SEQ ID NO: 42); triple mutant (3M) forward, 5'-CGGTGTCGTGGCCGGGACGCGGCGTCG-GCAGGCCTCTCAGGTCTC-3' (SEQ ID NO: 43) and reverse, 5'-GAGACC TGAGAGGCCTGCCGACGC-CGCGTCCGGCCACGACACCG-3' (SEQ ID NO: 44). The R93A mutant was used as a PCR template to generate the triple mutant (3M). Successful mutagenesis was confirmed by DNA sequencing.

Protein purification. Recombinant CTRP12 and its R93A mutant and triple mutant (3M) were produced and purified as follows. In brief, GripTite™ 293 cells (Invitrogen) were transfected with pcDNA3.1 encoding a C-terminal FLAG-tagged CTRP12 and its single or triple mutants using calcium phosphate method. To generate gCTRP12, we cloned the entire globular isoform (corresponding to residue 92-308) downstream of the endogenous signal peptide (residue 1-21). Supernatants (serum-free Opti-MEM; Invitrogen) of cells were collected and subjected to affinity chromatography using anti-FLAG® M2 Affinity Gel (Sigma) according to the manufacturer's protocol. Protein was eluted with 100 μg/ml FLAG peptide in PBS buffer. Protein was dialyzed against HEPES buffer (20 mM HEPES, 135 mM NaCl, pH 8.0) in a 10 kDa cut-off Slide-A-Lyzer dialysis cassette (Thermo Scientific), concentrated using a 10 kDa cut-off Amicon Ultra centrifugal filter (Millipore), aliquoted, and stored at −80° C. Protein concentration was determined using the Coomassie Plus™ Protein Assay Reagent (Thermo Scientific).

Gel filtration chromatographic analysis. Supernatants (500 μl) from transfected HEK 293 cells containing FLAG-tagged CTRP12 (WT), gCTRP12, R93A mutant, and triple mutant (3M) were sequentially loaded onto an AKTA FPLC and fractionated through a 10/300 Superdex 200 column (GE health science, Pistcataway, N.J., USA) in PBS. The collected fractions (0.5 ml each) were subjected to Western blot analysis using the anti-FLAG antibody.

Statistics. All statistical analyses were performed using two-tailed Student's t test in Excel. $p<0.05$ was considered significant. All quantification results with error bars are expressed as mean±SEM.

Example 1

Identification of CTRP12 as an adipokine. Mouse CTRP12 (GenBank: AAY21936.1; SEQ ID NO:2) was identified in silico as possessing a globular C1q/TNF-like domain, the signature domain of CTRPs. Limited sequence similarity to other CTRPs, including adiponectin (21% identity) and C1q (~20% identity), make it a distantly-related member. CTRP12 is evolutionarily conserved (FIG. 9 and Table 1) and has four basic domains (FIG. 1A). CTRP12 has a protease cleavage motif, 90-KKSR-93, with the cleavage site mapped to Lys-91 by N-terminal sequencing (FIG. 1A, arrow). Recombinant CTRP12 secreted from transfected HEK 293 cells (FIG. 1B, lane 1), endogenous CTRP12 secreted from 3T3-L1 adipocytes (FIG. 1B, lane 2), and circulating CTRP12 in human and mouse sera all contain both the full-length fCTRP12 and the cleaved globular gCTRP12 (FIG. 1B, lanes 3 and 4, respectively). In circulating mouse and human sera, gCTRP12 is the predominant form (FIG. 1B, lane 3, 4; FIG. 1C). Circulating levels of CTRP12 vary depending on the genetic background of the mice (FIG. 1C).

Figure 10:
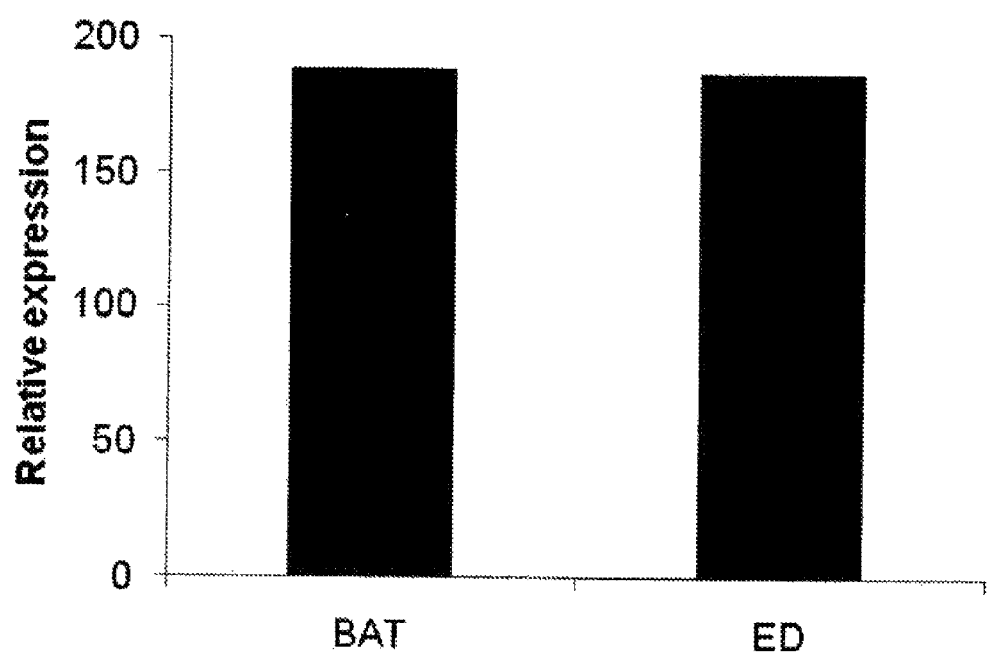
FIG. 10 illustrates the relative expression levels of CTRP12 in white and brown adipose tissue. The expression level of CTRP12 in each tissue is normalized against the level of 18 S rRNA. BAT, brown adipose tissue. ED, epididymal (white) adipose tissue.

In mice, CTRP12 is more widely expressed (FIG. 1D). In humans, it is expressed predominantly by adipose tissue (FIG. 1E); mouse white and brown adipose tissues express comparable amounts of CTRP12 (FIG. 10). The higher expression of human CTRP12 mRNA in adipose tissue correlates with its higher serum levels (FIG. 1B, lane 3). CTRP12 is highly induced during adipogenesis (FIG. 1F). Additionally, insulin increases both transcript (FIG. 1G) and protein levels of CTRP12 in adipocytes (FIG. 1H-I). Interestingly, administration of rosiglitazone, a pro-adipogenic and an insulin-sensitizing drug (14, 15), also increases the expression of CTRP12 in adipocytes (FIG. 1J). In contrast, both the mRNA and serum levels of CTRP12 are suppressed in insulin-resistant obese (ob/ob) mice (FIG. 1K-L). These results indicate that CTRP12 expression is positively regulated by insulin and rosiglitazone, and is dysregulated under the condition of obesity.

TABLE 1

Conservation of CTRP12 sequences in different vertebrate species. The unknown full-length sequence of platypus CTRP12 is indicated by "?". Amino acid identity to mouse CTRP12

| | Full-length | C1q/TNF-like domain |
|---|---|---|
| Mouse (*Mus musculus*) | 100 | 100 |
| Human (*Homo sapiens*) | 70 | 82 |

TABLE 1-continued

Conservation of CTRP12 sequences in different vertebrate species. The unknown full-length sequence of platypus CTRP12 is indicated by "?". Amino acid identity to mouse CTRP12

| | Full-length | C1q/TNF-like domain |
|---|---|---|
| Cow (*Bos taurus*) | 69 | 78 |
| Horse (*Equus caballus*) | 73 | 83 |
| Chicken (*Gallus gallus*) | 57 | 70 |
| Frog (*Xenopus laevis*) | 55 | 68 |
| Platypus (*Ornithorhynchus anatinus*) | ? | 72 |
| Zebra fish (*Danio rerio*) | 52 | 67 |

Example 2

Figure 11:
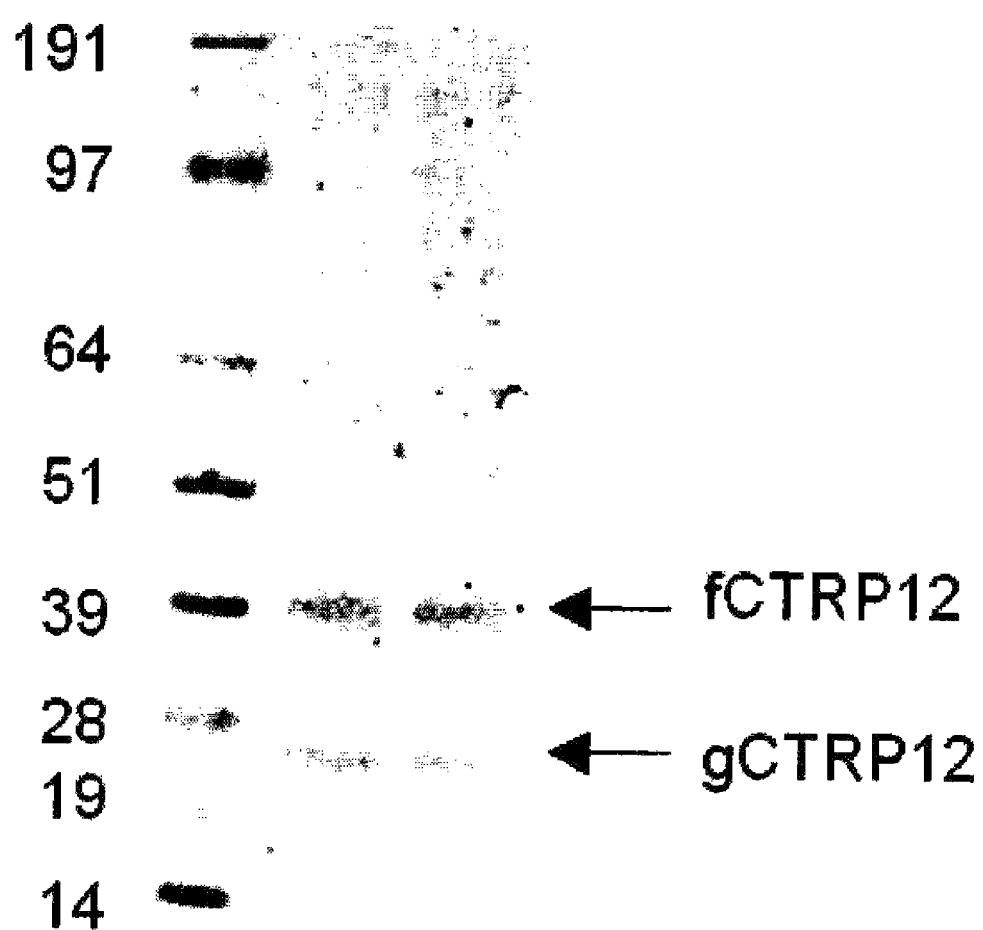
FIG. 11 shows the Coomassie blue stain of purified recombinant CTRP12 on an SDS-PAGE gel. HEK 293T cells were transfected with pcDNA3.1 encoding a C-terminal FLAG-tagged CTRP12. CTRP12 were purified using ANTI-FLAG® M2 Affinity Gel (sigma) according to the manufacturer's protocol

CTRP12 decreases blood glucose in mice. To determine the metabolic functions regulated by CTRP12, recombinant CTRP12 was administered to wild-type C57BL/6 mice and examined chCTRP12es in glucose dynamics. Secreted recombinant CTRP12 containing both fCTRP12 and gCTRP12 was affinity-purified from the supernatant of transfected HEK 293 cells (FIG. 11). Intraperitoneal (i.p.) injection of CTRP12 at a dose of 3.5 µg/g body weight into wild-type mice resulted in an acute 40% increase in serum CTRP12 over the physiological level (FIG. 2A).

Figure 2:
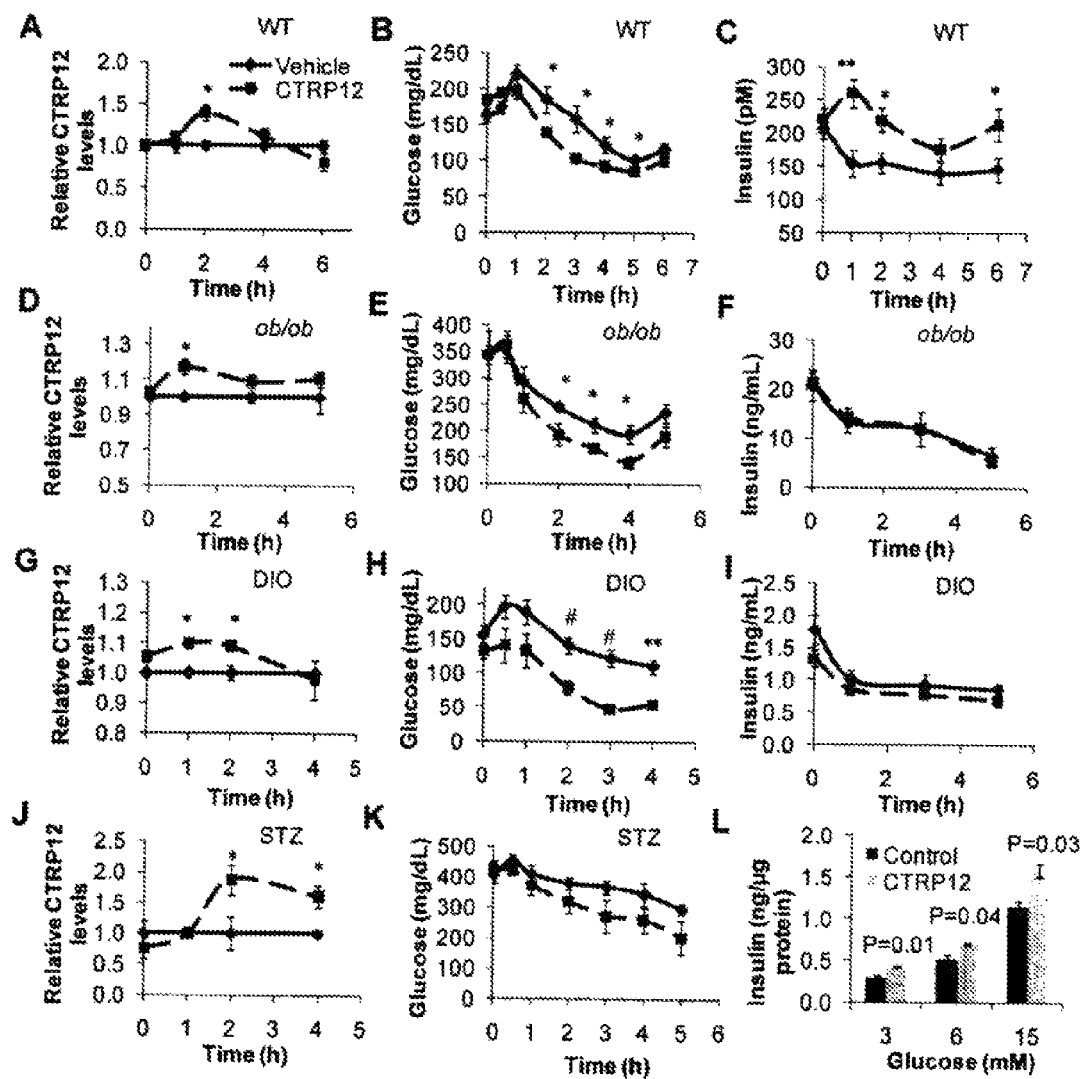
FIG. 2 depicts that recombinant CTRP12 lowers blood glucose in normal and diabetic mice. (A) Immunoblot quantification of serum CTRP12 levels following intraperitoneal (i.p.) injection of vehicle control or CTRP12 (3.5 µg/g body weight) into C57BL/6 mice (male, 9-wk-old, n=3). (B-C) Blood glucose (B) and serum insulin levels (C) of wild-type C57BL/6 mice over time following i.p. injection of vehicle control or CTRP12 (n=8). (D) Immunoblot quantification of serum CTRP12 levels following i.p. injection of vehicle control or CTRP12 (1.5 µg/g body weight) into ob/ob mice (male, 9-wk-old, n=3). (E-F) Blood glucose (E) and serum insulin levels (F) of ob/ob mice over time following i.p. injection of vehicle control or CTRP12 (n=6). (G) Immunoblot quantification of serum CTRP12 levels following i.p. injection of vehicle control or CTRP12 (1.5 µg/g body weight) into DIO mice (male, 20-wk-old, 14 weeks on high-fat diet, n=3). (H-I) Blood glucose (H) and serum insulin levels (I) of DIO mice over time following i.p. injection of vehicle control or CTRP12 (n=6). (J) Immunoblot quantification of serum CTRP12 levels following i.p. injection of vehicle control or CTRP12 (3 µg/g body weight) into streptozotocin (STZ)-treated C57BL/6 mice (male, 7-wk-old, n=3). (K) Blood glucose of STZ-treated mice after i.p. injection of vehicle control or CTRP12 (n=5). (L) CTRP12 (10 µg/mL, 2-hr incubation) increases insulin secretion from INS-1 cells at low, medium, and high glucose levels (n=3). All data are expressed as mean±SEM. (#) $p<0.001$; (**) $p<0.01$; (*) $p<0.05$.
Figure 12:
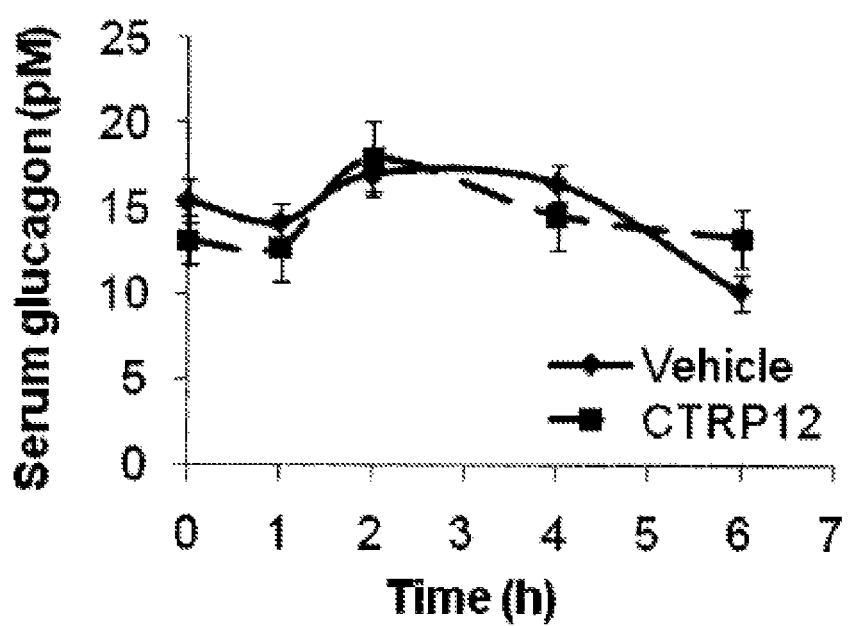
FIG. 12 illustrates the serum glucagon in wild-type mice injected with vehicle control or CTRP12.

Concomitantly, there was a significant lowering in blood glucose with a maximum 40% decrease in CTRP12-treated wild-type mice (FIG. 2B). Surprisingly, there was a maximum 70% increase in serum insulin after CTRP12 administration (FIG. 2C). The rise in insulin appeared to be biphasic (FIG. 2C), reminiscent of the biphasic kinetics of glucose-stimulated insulin secretion, despite temporal differences. This biphasic rise in insulin suggests that the chCTRP12es in insulin levels induced by CTRP12 are more likely due to an increase in insulin secretion rather than a decrease in insulin clearance. Indeed, in rat pancreatic β-cells (INS-1), CTRP12 potentiated glucose-stimulated insulin secretion at low, intermediate, and high glucose concentrations (FIG. 2L). In contrast, glucagon levels remained unchCTRP12ed between the two groups (FIG. 12).

Next, it was tested whether CTRP12 can lower blood glucose in mouse models of diabetes. Three diabetic mouse models were used—leptin-deficient ob/ob mice, diet-induced obese (DIO) mice, and streptozotocin (STZ)-treated mice—all of which are on the C57BL/6 background. In ob/ob mice, i.p. administration of CTRP12 at a dose of 1.5 µg/g body weight caused a 20% increase in serum CTRP12 over baseline levels (FIG. 2D). This changes was accompanied by a 25% decrease in blood glucose levels over a 2-hour period (FIG. 2E). Further, insulin levels remained unchCTRP12ed in ob/ob mice injected with CTRP12 (FIG. 2F), compared to vehicle-injected mice.

Administration of CTRP12 (1.5 µg/g body weight) to DIO mice fed a high-fat diet for 14 weeks caused a modest increase in the serum level of CTRP12 (FIG. 2G). However, the glucose-lowering effect of CTRP12 was much more potent in DIO mice, with a maximum 70% decrease in blood glucose levels in the CTRP12-treated group (FIG. 2H). At 3 hours and beyond, DIO mice injected with CTRP12 had blood glucose levels of ~50 mg/dL (FIG. 2H), well below the normal fasting blood glucose concentration in mice (90-100 mg/dL). As with ob/ob mice, DIO mice injected with CTRP12 showed no chCTRP12es in insulin levels (FIG. 2I). In STZ-treated mice, i.p. administration of CTRP12 at a dose of 3 µg/g body weight caused a ~100% increase in serum CTRP12 levels compared to vehicle-injected controls (FIG. 2J). However, despite a strong trend toward lower blood glucose levels, the decrease in blood glucose in CTRP12-injected mice was not statistically significant at any time point (FIG. 2K). The inability of CTRP12 to significantly lower blood glucose in STZ-treated mice may reflect the severe degree of hyperglycemia seen in these animals. Alternatively, insulin may be permissive in the glucose-lowering of CTRP12, since STZ-treated mice are essentially devoid of insulin due to the destruction of pancreatic β-cells.

Example 3

Figure 3:
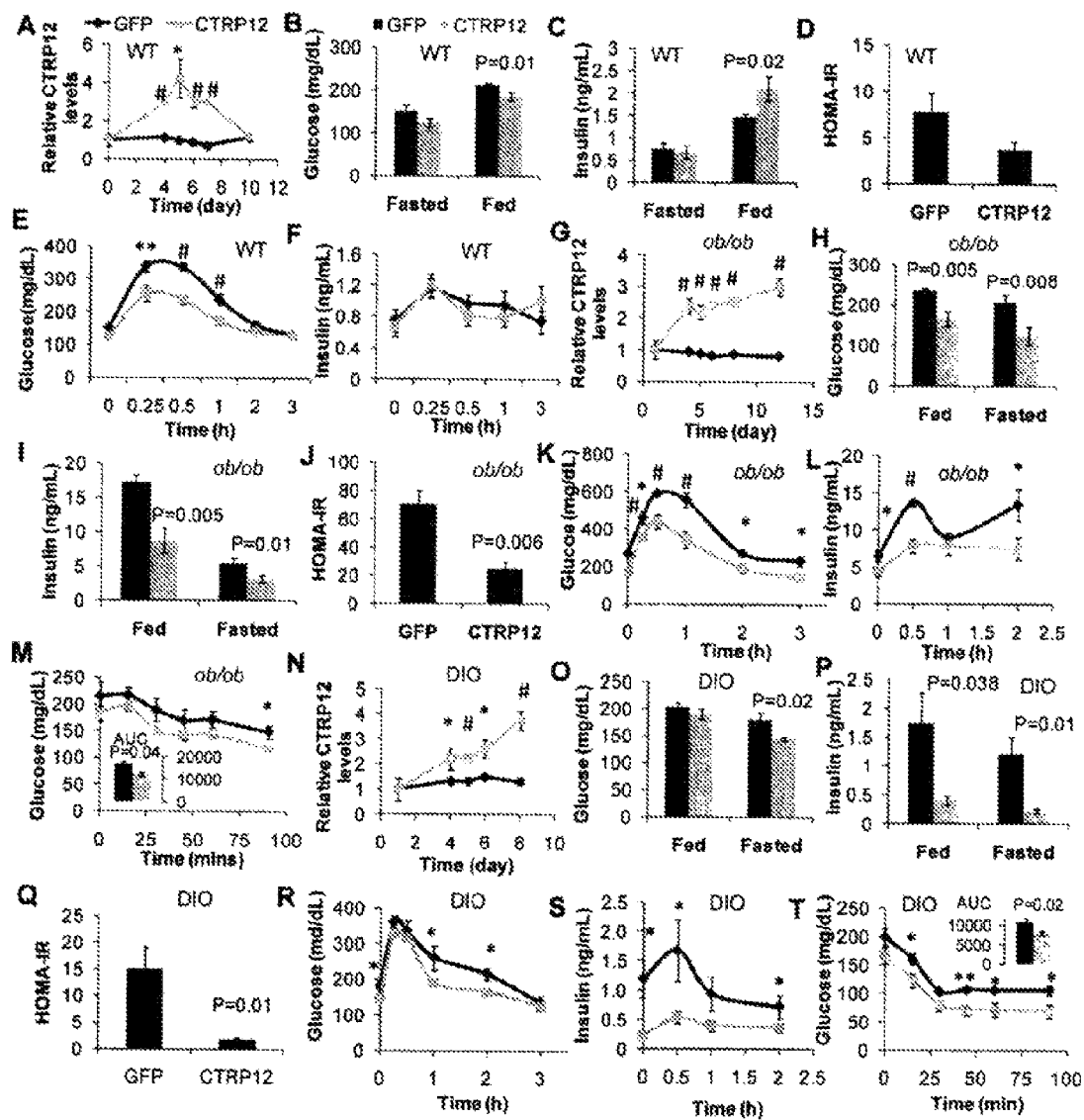
FIG. 3 shows that CTRP12 improves insulin sensitivity in ob/ob and DIO mice. (A) Immunoblot quantification of serum CTRP12 levels following tail vein injection of adenovirus into WT C57BL/6 mice (male, 9-wk-old, n=3). (B-C) Fasting and fed glucose (B) and insulin (C) levels of GFP- or CTRP12-expressing WT mice (n=8-9). (D) HOMA-IR index of WT mice expressing GFP or CTRP12. (E) GTT of WT mice expressing GFP (n=8) or CTRP12 (n=9). (F) Serum insulin levels during the course of GTT (n=8-9). (G) Immunoblot quantification of serum CTRP12 levels following adenovirus injection into ob/ob mice (male, 10-wk-old, n=3). (H-I) Fasting and fed glucose (H) and insulin (I) levels of GFP- or CTRP12-expressing ob/ob mice (n=6). (J) HOMA-IR index of ob/ob mice expressing GFP or CTRP12 (n=6). (K) GTT of ob/ob mice expressing GFP or CTRP12 (n=6). (L) Serum insulin levels during the course of GTT in ob/ob mice expressing GFP or CTRP12 (n=6). (M) Blood glucose levels and area-under-curve (AUG) of glucose in the ITT in ob/ob mice expressing GFP or CTRP12 (n=6). (N) Immunoblot quantification of serum CTRP12 levels following adenovirus injection into DIO mice (male, 20-week-old, n=3). (O-P) Fasting and fed glucose (O) and insulin (P) levels of GFP- or CTRP12-expressing DIO mice (n=6). (Q) HOMA-IR index of DIO mice expressing GFP or CTRP12. (R) GTT of DIO mice expressing GFP or CTRP12 (n=6). (S) Serum insulin levels during the course of GTT in DIO mice expressing GFP or CTRP12 (n=6). (T) Blood glucose levels and AUC in the ITT in DIO mice expressing GFP or CTRP12 (n=6). All data are expressed as mean±SEM. (#) $p<0.001$; (**) $p<0.01$; (*) $p<0.05$.
Figure 13:
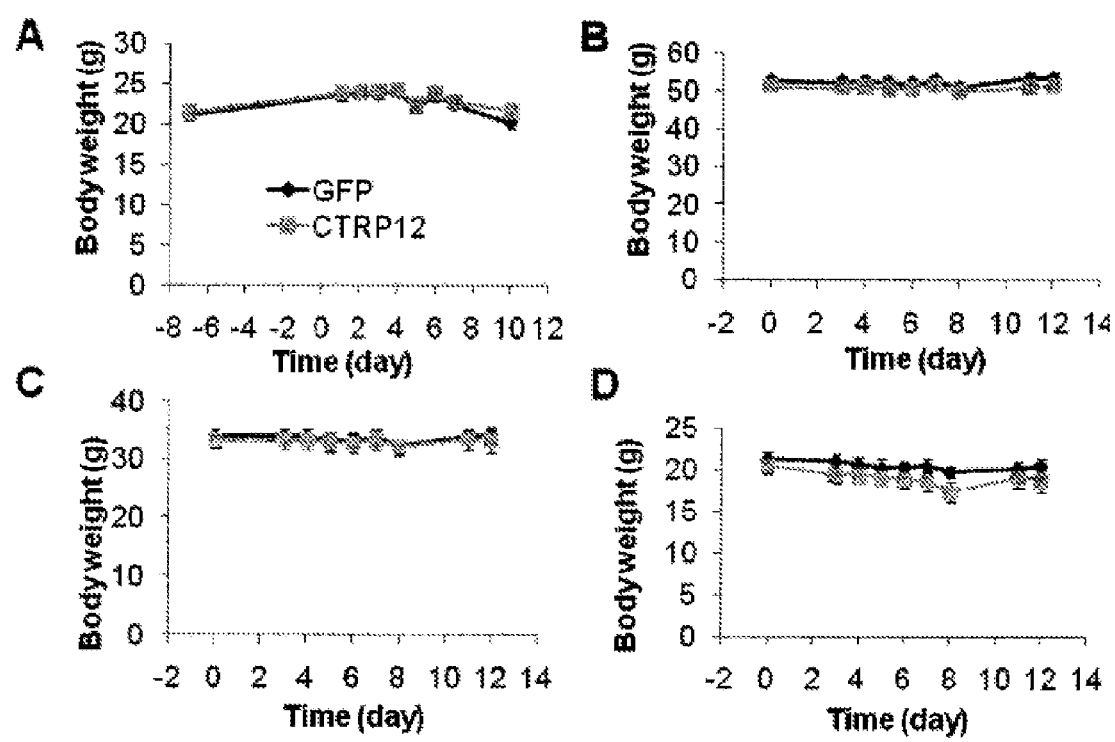
FIG. 13 (A-D) shows body weights of wild-type (A), ob/ob (B), DIO (C), and STZ-treated (D) C57BL/6 mice injected with adenovirus expressing either GFP or CTRP12. Adenovirus encoding GFP or CTRP12 was administered on day 0.
Figure 14:
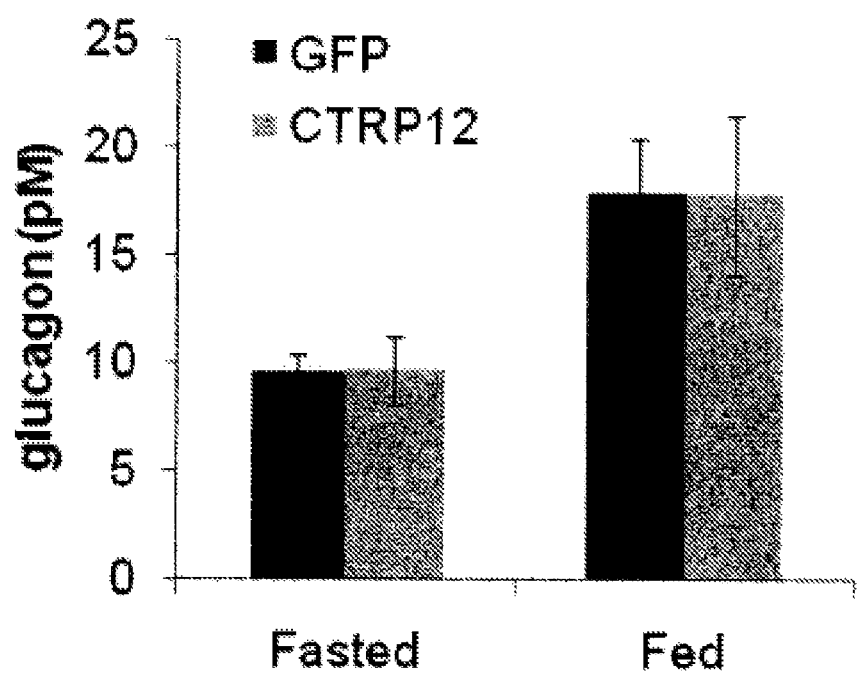
FIG. 14 illustrates the serum glucagon levels of GFP- and CTRP12-expressing wild-type mice in fed and fasted states.

CTRP12 enhances insulin sensitivity in mice. The metabolic consequences of short-term ectopic expression of CTRP12 in mice using adenoviral vectors was investigated. Adenoviral-mediated expression of CTRP12 did not result in body weight chCTRP12es compared to GFP-expressing mice over the course of the experiment (FIG. 13). In wild-type C57BL/6 mice, expression of CTRP12 caused a maximum 3-fold elevation of serum CTRP12 levels (FIG. 3A). Blood glucose levels were 20 mg/dl lower in the fed state in CTRP12-expressing mice (FIG. 3B) but were not significantly different in the fasted state. Serum insulin levels in these mice were ~45% higher in the fed state (FIG. 3C), but were not different in the fasted state (FIG. 3C). The fasted and fed glucagon levels were not different between the two groups (FIG. 14).

Figure 15:
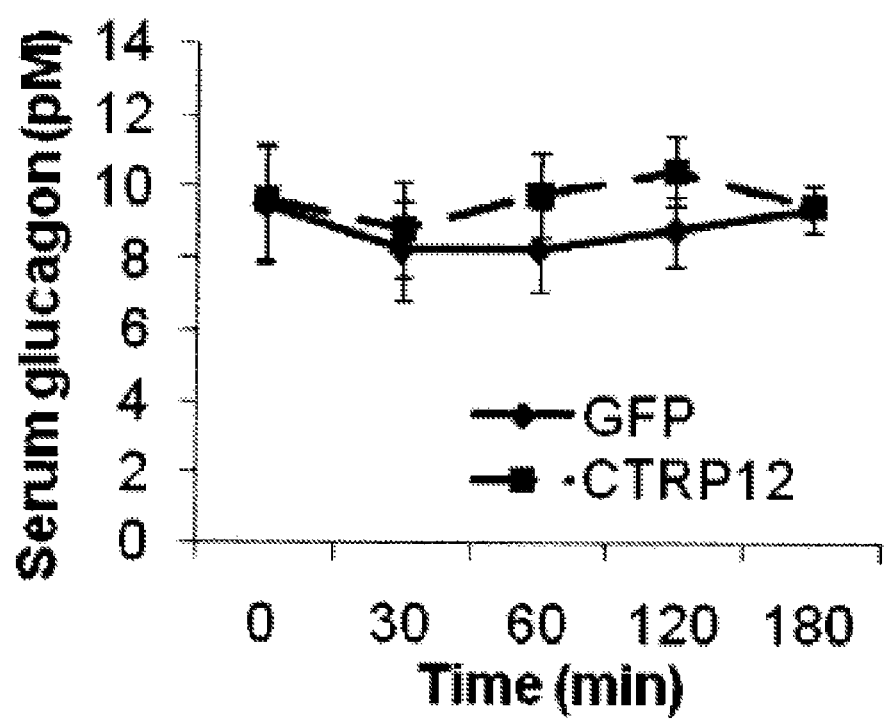
FIG. 15 illustrates the glucagon levels during the GTT test in wild-type mice expressing GFP or CTRP12.

Assessment of whole-body insulin sensitivity using the homeostatic model assessment insulin resistance index (HOMA-IR) revealed a trend toward a decreased insulin resistance index in CTRP12-expressing mice (FIG. 3D). Consistent with this, wild-type mice expressing CTRP12 showed a much faster rate of glucose disposal over time in a glucose tolerance test (GTT) (FIG. 3E), despite no chCTRP12es in insulin or glucagon levels during the GTT (FIGS. 3F and 15). In ob/ob mice, expression of CTRP12 resulted in a 2-fold increase of serum CTRP12 levels over GFP-expressing mice (FIG. 3G). The fed and fasted (7 hour) glucose and insulin levels in ob/ob mice expressing CTRP12 were much lower compared to mice expressing control GFP (FIG. 3H,I). The significant reduction in the fasted blood glucose and insulin levels in ob/ob mice indicated decreased insulin resistance, as reflected by the HOMA-IR index (FIG. 3J). Consistent with improved insulin sensitivity, ob/ob mice expressing CTRP12 had a much faster rate of glucose disposal in a GTT (FIG. 3K), with significantly lower insulin levels over the course of the experiment (FIG. 3L). In an insulin tolerance test (ITT), ob/ob mice expressing CTRP12 had overall lower blood glucose levels, as reflected by a smaller area-under-the-curve (AUC), again indicating improved insulin sensitivity in these mice (FIG. 3M).

Figure 16:
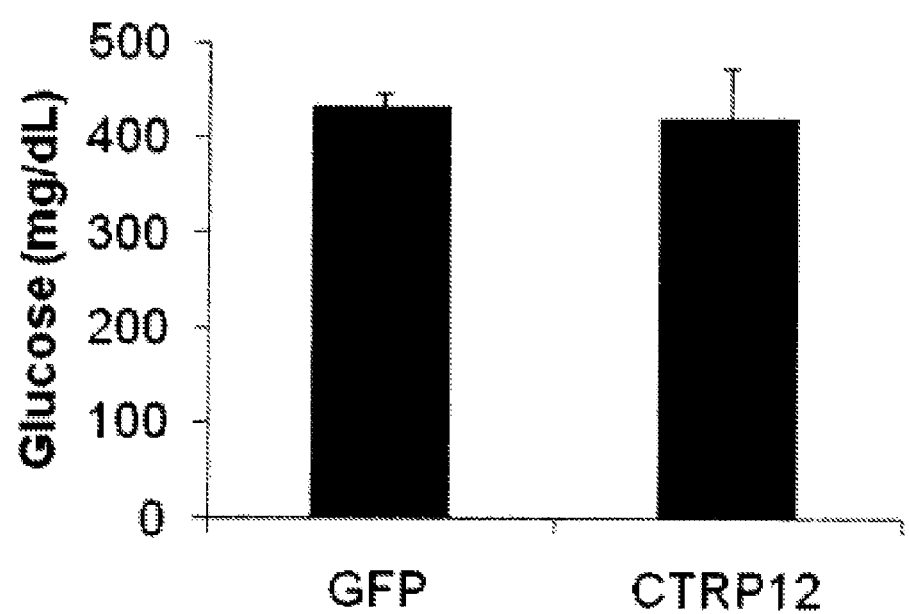
FIG. 16 illustrates the adenovirus-mediated CTRP12 expression does not lower glucose levels in STZ-treated mice.
Figure 17:
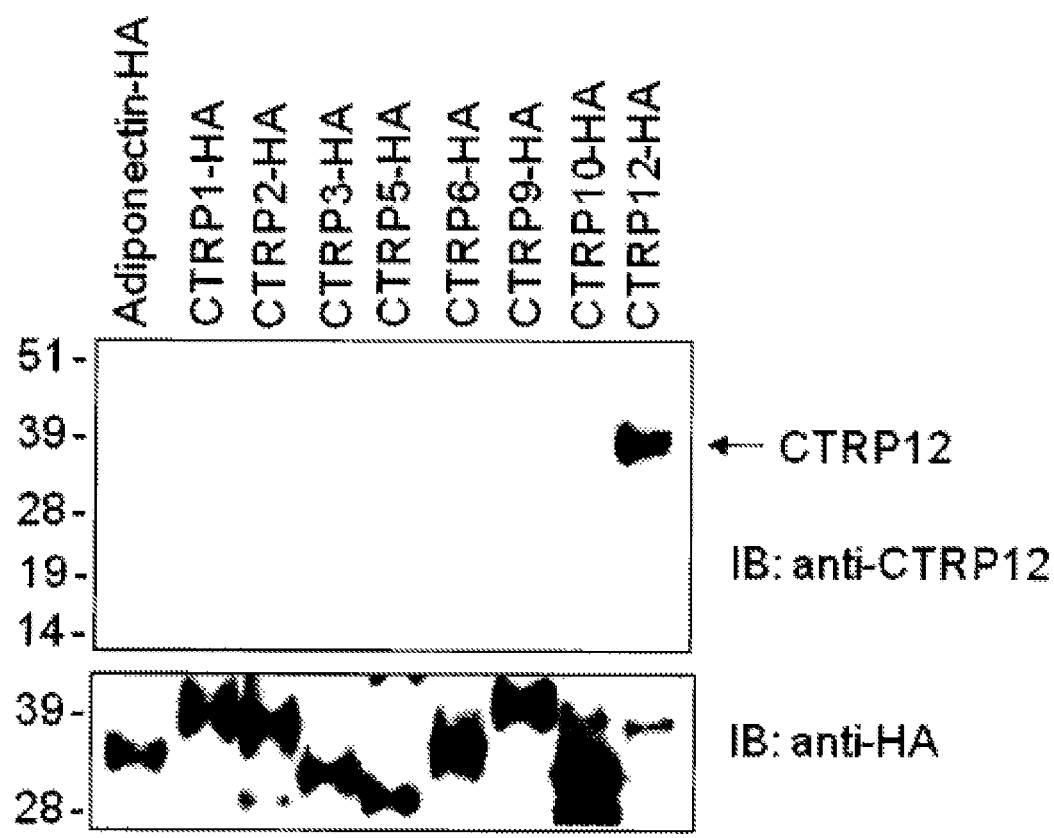
FIG. 17 shows the Western blot analysis of recombinant CTRP proteins showing the specificity of anti-CTRP12 antibody.

In DIO mice, the adenoviral vector achieved a 2- to 3-fold increase in serum CTRP12 levels over GFP-expressing mice (FIG. 3N). DIO mice expressing CTRP12 had lower fasted (7 hour) blood glucose levels (FIG. 3O) and significantly lower fed and fasted insulin levels (FIG. 3P). The reduction in fasted blood glucose and insulin levels in DIO mice expressing CTRP12 resulted in greatly reduced HOMA-IR index (FIG. 3Q). Consistent with improved insulin sensitivity, DIO mice expressing CTRP12 showed a greater rate of glucose disposal with considerably lower insulin levels in a GTT (FIGS. 3R, 3S). In addition, DIO mice expressing CTRP12 had lower blood glucose levels in an insulin tolerance test (FIG. 3T), again reflecting enhanced insulin sensitivity. In contrast to the ob/ob and DIO mice, expression of CTRP12 did not result in lowering of blood glucose in the STZ-treated mice (FIG. 16).

Example 4

Figure 4:
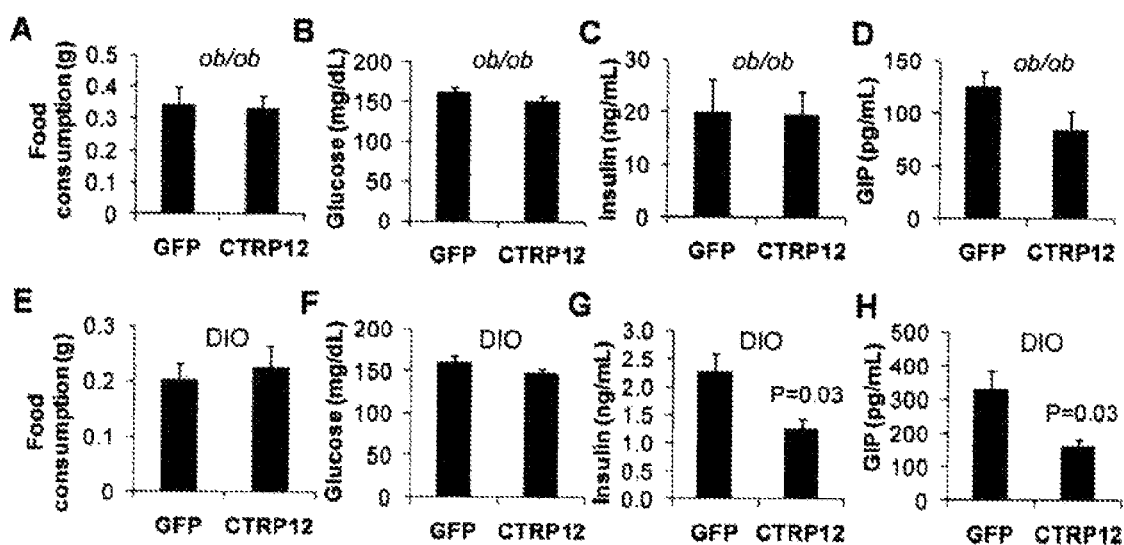
FIG. 4 depicts data that CTRP12 reduces postprandial insulin resistance in DIO mice. Food intake (A), blood glucose (B), insulin (C), and GIP (D) levels in GFP- or CTRP12-expressing ob/ob mice (n=6/group) in the re-fed state. Food intake (E), blood glucose (F), insulin (G), and GIP (H) levels in GFP- or CTRP12-expressing DIO mice (n=6/group) in the re-fed state. All data are expressed as mean±SEM. DIO, diet-induced obese; GIP, glucose-dependent insulinotropic polypeptide.

CTRP12 reduces postprandial insulin resistance in DIO mice. To extend the physiological analyses of CTRP12 and to assess whether CTRP12 has a role in postprandial physiology, a meal tolerance test in ob/ob and DIO mice expressing control GFP or CTRP12 was performed. Mice were fasted overnight and then given unlimited access to food for 1 hour in the re-feeding phase. No difference was observed in food intake in the re-feeding period between the GFP- and CTRP12-expressing ob/ob mice (FIG. 4A). Blood glucose levels in the re-fed state were not different between the two groups of ob/ob mice (FIG. 4B). Serum levels of insulin and glucose-dependent insulinotropic peptide (GIP), a gut-derived incretin hormone, were also not significantly different in the re-fed state (FIGS. 4C, 4D). In DIO mice expressing GFP or CTRP12, no difference in food intake was observed in the 1 hour re-fed period (FIG. 4E). Despite similar blood glucose levels (FIG. 4F), DIO mice expressing CTRP12 had much lower insulin levels in the re-fed state (FIG. 4G), indicating a decrease in postprandial insulin resistance in these mice. A notable reduction (~50%) in GIP levels was also observed in DIO mice expressing CTRP12 (FIG. 4H). Since GIP promotes postprandial insulin secretion from pancreatic β-cells, a decrease in GIP levels may have contributed to the marked reduction in insulin levels seen in the re-fed state in CTRP12-expressing DIO mice (FIG. 4G).

Example 5

Figure 5:
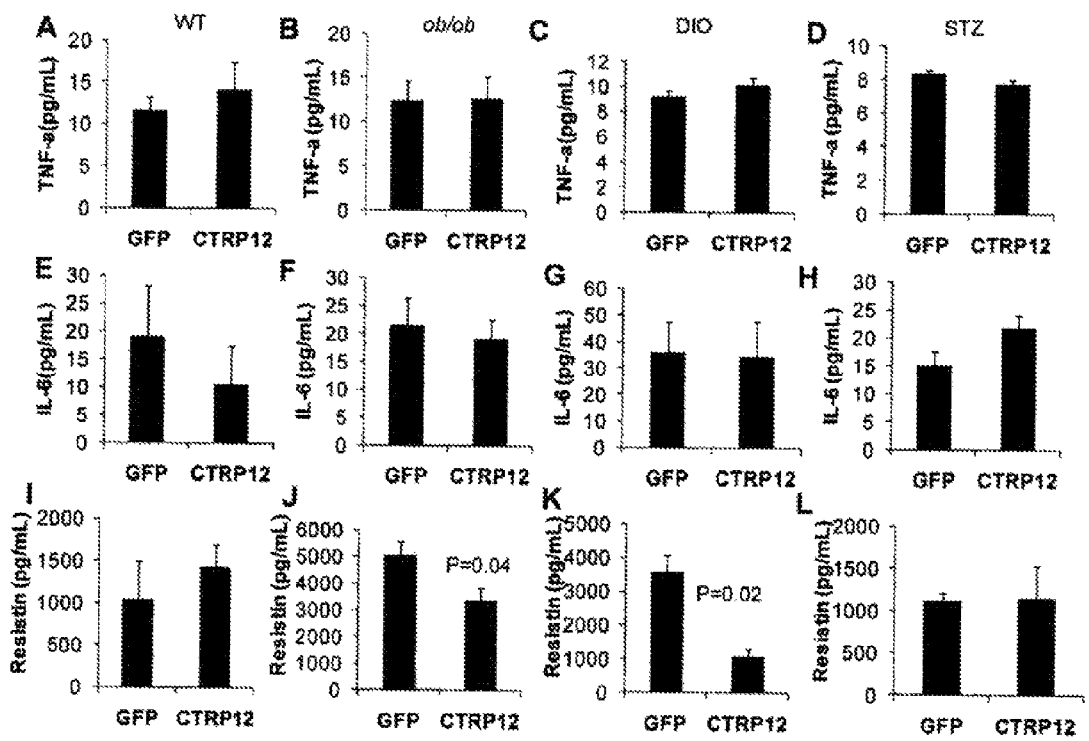
FIG. 5 provides evidence that CTRP12 reduces serum resistin levels in ob/ob and DIO mice. (A-D) serum TNF-α levels in the WT (A, n=8-9), ob/ob (B, n=6), DIO (C, n=6), and STZ-treated mice (D, n=5) expressing GFP or CTRP12. (E-H) Serum IL-6 levels in the WT (E, n=8-9), ob/ob (F, n=6), DIO (G, n=6), and STZ-treated mice (H, n=5) expressing GFP or CTRP12. (I-L) Serum resistin levels in the WT (I, n=8-9), ob/ob (J, n=6), DIO (K, n=6), and STZ-treated mice (L, n=5) expressing GFP or CTRP12. All data are expressed as mean±SEM.

Diabetic mice expressing CTRP12 have lower resistin levels associated with insulin resistance. Chronic low-grade inflammation is tightly associated with and may underlie the insulin-resistant state. Thus, to test if CTRP12 reduced insulin resistance through its potential anti-inflammatory actions, serum levels of two key inflammatory cytokines, TNF-α and IL-6, were measured in mice expressing control GFP or CTRP12. As shown in FIGS. 5A-H, CTRP12 did not lower circulating levels of TNF-α and IL-6 in wild-type, ob/ob, DIO, or STZ-treated mice. Consistent with the serum levels, expression of TNF-α and IL-6 mRNAs in the adipose tissue were also not different between the GFP- and CTRP12-expressing mice (data not shown). In contrast to TNF-α and IL-6, serum levels of resistin, an adipokine known to induce insulin resistance and promote inflammation, were significantly reduced in ob/ob and DIO mice expressing CTRP12 (FIGS. 5J, 5K), and this could partially account for decreased insulin resistance seen in these mice. In contrast to ob/ob and DIO mice, expressing CTRP12 in wild-type and STZ-treated mice did not alter resistin levels (FIGS. 5I and 5L).

Example 6

Figure 6:
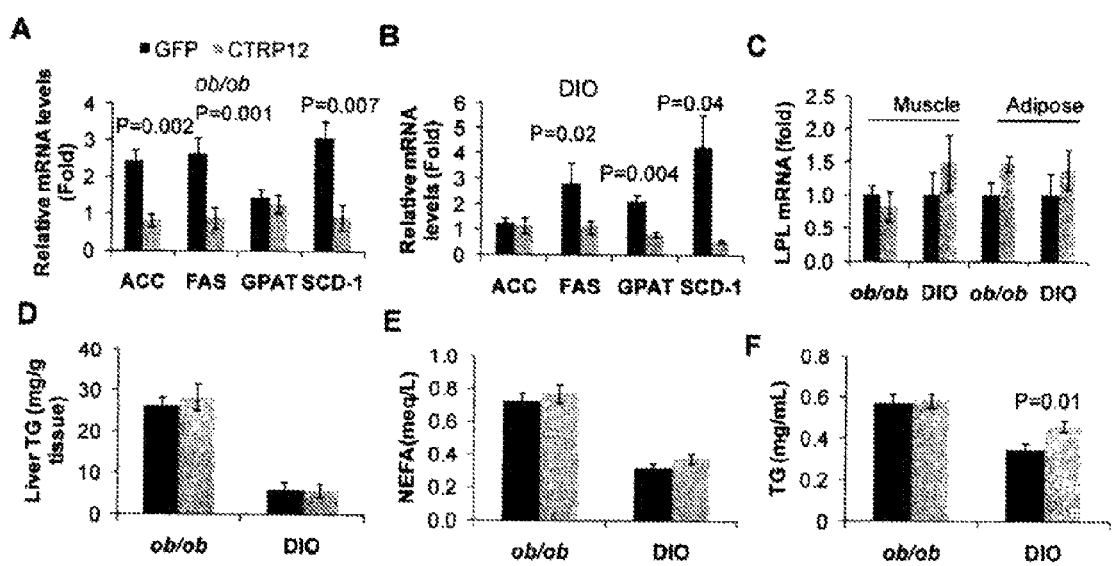
FIG. 6 shows that CTRP12 suppresses hepatic lipogenic program. (A-B) Expression of hepatic ACC, FAS, GPAT, and SCD-1 mRNA levels in ob/ob (A) and DIO (B) mice expressing GFP (n=6) or CTRP12 (n=6). (C) Expression of LPL mRNA levels in the muscle and adipose tissue of ob/ob and DIO mice expressing GFP (n=6) or CTRP12 (n=6). Liver TG contents (D), serum NEFA (E) and TG levels (F) in ob/ob and DIO mice expressing GFP (n=6) or CTRP12 (n=6). All data are expressed as mean±SEM. TG, triacylglycerol; ACC, acetyl-CoA carboxylase; FAS, fatty acid synthase; GPAT, Glycerol-3-phosphate acyltransferase; SCD-1, stearoyl-CoA desaturase-1; LPL, lipoprotein lipase.

CTRP12 suppresses hepatic lipogenic program. Ectopic accumulation of lipids in non-adipose tissue such as liver and muscle is a mechanism causing insulin resistance. Several known insulin-sensitizing molecules reduce insulin resistance in part through modulating lipid metabolism—for example, by enhancing fatty acid oxidation and/or reducing fatty acid synthesis—leading to lower serum non-esterified fatty acid (NEFA) and/or lipid deposition in non-adipose tissue. To further explore the mechanism by which CTRP12 improves insulin sensitivity, its role in regulating lipid metabolism was assessed. In ob/ob and DIO mice, expression of CTRP12 suppressed the expression of major lipogenic enzyme genes in the liver, including acetyl-CoA carboxylase (ACC), fatty acid synthase (FAS), glycerol phosphate acyl-transferase (GPAT), and stearoyl-CoA desaturase-1 (SCD-1) (FIGS. 6A, 6B). In contrast, the expression of lipoprotein lipase (LPL) mRNA in muscle and adipose tissue were not different between the GFP- and CTRP12-expressing mice (FIG. 6C). Despite significant reduction in the expression of hepatic lipogenic genes, no significant differences were observed in hepatic triacylglycerol (TG) content (FIG. 6D) and serum NEFA levels (FIG. 6E) between GFP- and CTRP12-expressing mice. Interestingly, serum TG levels in CTRP12-expressing DIO mice showed a modest increase compared to GFP-expressing mice (FIG. 6F). A short-term expression of CTRP12 may not be of sufficient duration to significantly impact liver TG content despite significant reductions in hepatic lipogenic gene expression.

Example 7

Figure 7:
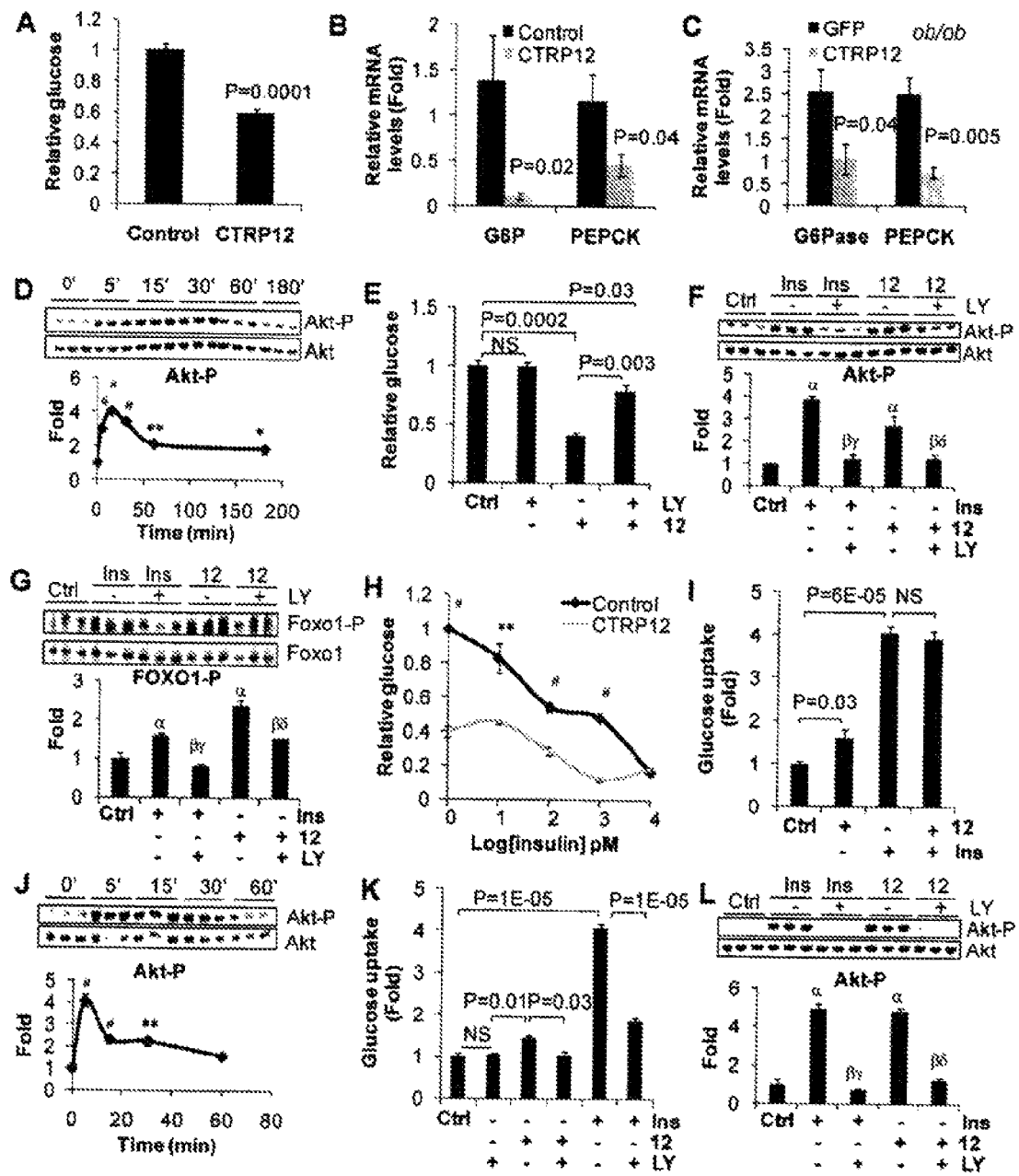
FIG. 7 illustrates that CTRP12 activates the PI3K-Akt signaling pathway to regulate glucose metabolism. (A) CTRP12 (10 µg/mL, 24-hour incubation) decreases gluconeogenesis in rat H4IIE hepatocytes (n=3). (B) CTRP12 (10 µg/mL, 24-hour incubation; n=6) decreases the expression of gluconeogenic enzymes, G6Pase and PEPCK. (C) G6Pase and PEPCK mRNA levels are decreased in the liver of ob/ob mice expressing CTRP12 (n=6). Expression values are normalized against β-actin transcript levels. (D) Time course of Akt phosphorylation at Thr-308 induced by CTRP12 treatment (10 µg/mL). (E) Suppression of gluconeogenesis by CTRP12 (10 µg/mL, 24-hr incubation) in H4IIE hepatocytes is inhibited by LY-294002 (20 µM, 2our-hr co-incubation). (F-G) The increase of Akt (Thr-308) (F) and Foxo-1 (Ser-256) (G) phosphorylation induced by CTRP12 (10 µg/mL) is inhibited by LY-294002 (20 µM). (H) Inhibition of gluconeogenesis in H4IIE hepatocytes by CTRP12 (10 µg/mL) in the presence of various concentrations of insulin. (I) CTRP12 (10 µg/mL) increases glucose uptake in 3T3-L1 adipocytes and is non-additive to that of 10 nM insulin treatment. (J) Time course of Akt (Thr-308) phosphorylation induced by CTRP12 treatment (10 µg/mL) in 3T3-L1 adipocytes. (K-L) The increase of glucose uptake (K) and Akt phosphorylation (Thr-308) (L) in 3T3-L1 adipocytes by CTRP12 (10 µg/mL) are inhibited by LY-294002 (50 µM). Ins, insulin (10 nM); LY, LY-294002; 12, recombinant CTRP12; G6Pase, glucose-6-phosphatase; PEPCK, phosphoenolpyruvate carboxykinase. All data are expressed as mean±SEM. (#) $p<0.001$; (**) $p<0.01$; (*) $p<0.05$. α, $p<0.05$ compared with control; β, not-significant compared with control; γ, $p<0.05$ compared with insulin; δ, $p<0.05$ compared with CTRP12.
Figure 8:
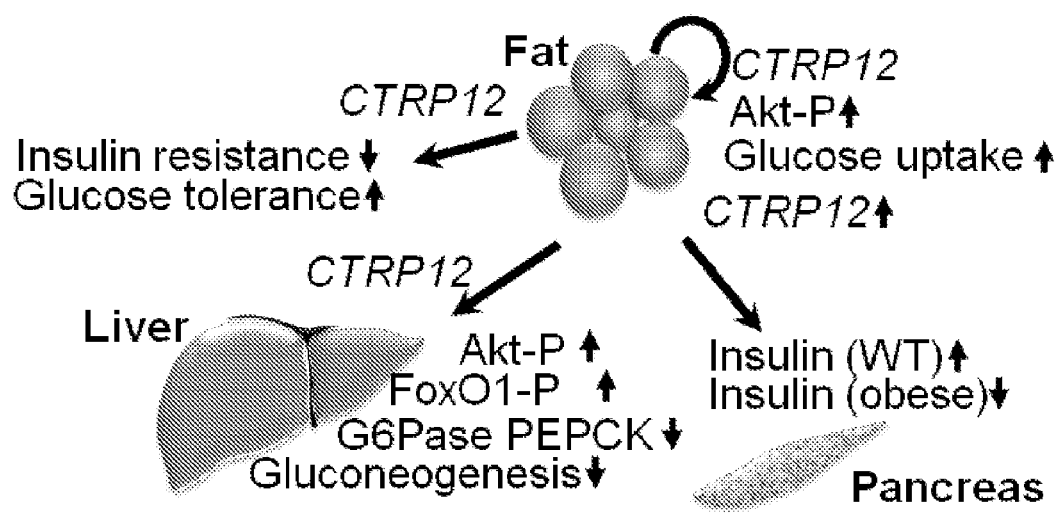
FIG. 8 is an illustration of a proposed model for CTRP12 function. CTRP12 is a novel adipose tissue-derived adipokine that acts on adipose tissue, liver, and pancreas to enhance whole-body glucose homeostasis. CTRP12 activates the Akt signaling pathway to suppress hepatic gluconeogenic gene expression and gluconeogenesis while promoting glucose uptake in adipocytes. CTRP12 lowers blood glucose, and reduces serum insulin and resistin levels in conditions of obesity and diabetes. Akt-P, Akt phosphorylation; Foxo-1-P, Foxo-1 phosphorylation. Small upward and downward arrows indicate increase and decrease, respectively. Big arrows indicate the target tissues and actions of CTRP12.

CTRP12 activates the PI3K-Akt signaling pathway to suppress gluconeogenesis and promote glucose uptake. To uncover the signaling pathways directly activated by CTRP12 and to address whether CTRP12 acts independently of insulin, insulin-responsive cell lines were utilized to investigate the mechanisms of action of CTRP12. In rat H4IIE hepatocytes, recombinant CTRP12 reduced gluconeogenesis (FIG. 7A) in the absence of insulin by suppressing the expression of two key gluconeogenic enzyme genes, glucose-6-phosphatase (G6Pase) and phosphoenolpyruvate carboxykinase (PEPCK; FIG. 7B). Consistent with the in vitro data, expression of CTRP12 in ob/ob mice also potently suppressed hepatic G6Pase and PEPCK mRNA expression (FIG. 7C). In the absence of insulin, recombinant CTRP12 rapidly induced Akt phosphorylation in H4IIE hepatocytes (FIG. 7D). A phosphoinositide 3-kinase (PI3K)-specific inhibitor, LY29004, alleviated the suppression of gluconeogenesis by CTRP12 (FIG. 7E), indicating that the PI3K-Akt pathway is at least partially responsible for the suppression of gluconeogenesis by CTRP12. Similarly, Akt activation by CTRP12 was inhibited by LY29004 in hepatocytes (FIG. 7F). Foxo1, a downstream target of Akt and an important regulator of hepatic gluconeogenesis, also showed increased phosphorylation in hepatocytes in response to CTRP12 treatment (FIG. 7G). This increase in phosphorylation was LY29004-sensitive, similar to insulin-induced Akt and Foxo-1 phosphorylation (FIGS. 7F, 7G). These results indicate that CTRP12 activates Akt through PI3K.

Example 8

A determination of whether CTRP12 synergizes with insulin at the cellular level to control hepatic gluconeogenesis was made. Incubation of H4IIE hepatocytes with insulin showed a 50% suppression of gluconeogenesis at the $IC_{50}$ concentration of ~100 pM (FIG. 7H). In the presence of recombinant CTRP12 we observed further inhibition of gluconeogenesis, but the $IC_{50}$ of insulin remained the same (FIG. 7H). This finding indicates that the suppression of gluconeogenesis by CTRP12 and insulin is additive rather than synergistic (FIG. 7H). Treatment of differentiated 3T3-L1 adipocytes with CTRP12 led to a modest increase in glucose uptake, and the increase is non-additive to that induced by 10 nM insulin (FIG. 7I), suggesting that CTRP12 possibly acts on the same signaling targets as insulin in adipocytes. Indeed, CTRP12 rapidly activated the Akt signaling pathway in 3T3-L1 adipocytes (FIG. 7J). The increase in glucose uptake and activation of Akt by CTRP12 in adipocytes were inhibited by LY29004 (FIGS. 7K-L), indicating that the PI3K-Akt signaling pathway mediates the effect of glucose uptake by CTRP12. These data demonstrate a direct role of CTRP12—independent of insulin—in regulating glucose metabolism in hepatocytes and adipocytes.

Example 9

Cleavage, glycosylation, and oligomerization of CTRP12. Mouse CTRP12 contains four recognizable domains, three potential N-linked glycosylation sites that conform to N-X-(S/T) motif, four Cys residues, and an endopeptidase cleavage motif, "KKXR", located in the N-terminus (FIG. 1A). These features suggest that the protein likely undergoes multiple types of posttranslational modification. Importantly, the four Cys residues, the cleavage motif, and one of the N-glycosylation sites (Asn-39) are highly conserved in divergent vertebrate species (FIG. 18; arrows).

Figure 19:
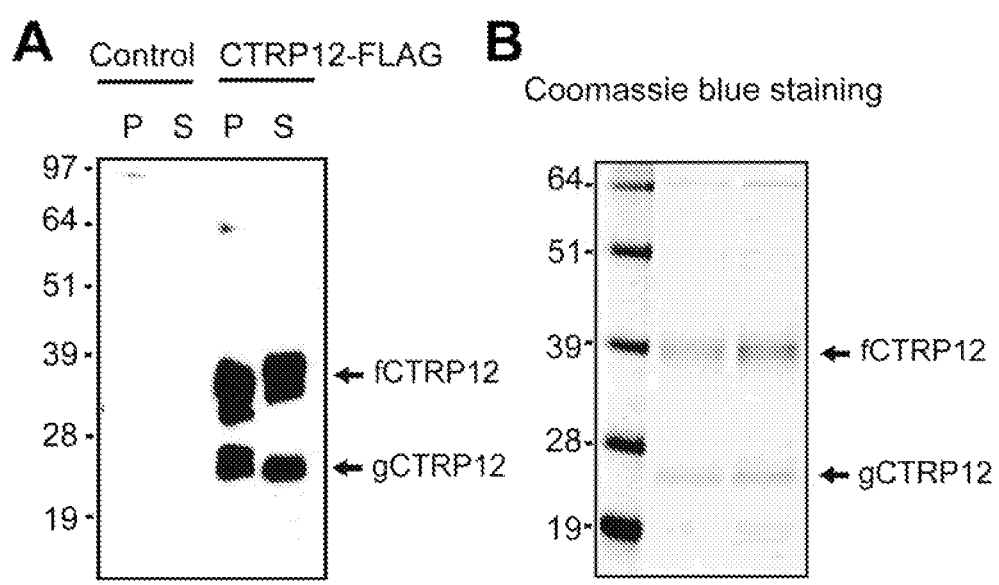
FIG. 19 shows that CTRP12 is a secreted multimeric glycoprotein. 19A is an immunoblot analysis of CTRP12 expressed in heterologous HEK 293T cells. Empty vector (pcDNA3.1) was used as negative control. P, pellet; S, supernatant. 19B shows Coomassie blue staining of purified recombinant CTRP12 on a SDS-PAGE gel.

Two isoforms of the protein, differing in size, were produced when FLAG epitope-tagged CTRP12 is expressed in heterologous mammalian HEK 293T cells (FIG. 19 A), indicating proteolytic processing of the recombinant CTRP12. Cleavage is physiologically relevant: endogenous CTRP12 secreted from differentiated 3T3-L1 adipocytes and CTRP12 circulating in human and mouse serum also exist in two isoforms—full-length fCTRP12 (~40 kDa) and a cleaved gCTRP12 (~25 kDa). In serum, gCTRP12 is the predominant isoform. Since both isoforms were found in cell pellet and supernatant of CTRP12-expressing HEK 293T cells, proteolytic processing most likely occurred inside the cell prior to protein secretion (FIG. 19A). N-terminal sequencing of purified mouse recombinant gCTRP12 (FIG. 19B) indicated that cleavage occurred at Lys-91, at the predicted endopeptidase cleavage site ($K^{90}K^{91}\downarrow X^{92}R^{93}$). Cleavage appears to be regulated; only a fraction of fCTRP12 is processed into gCTRP12.

Example 10

Figure 20:
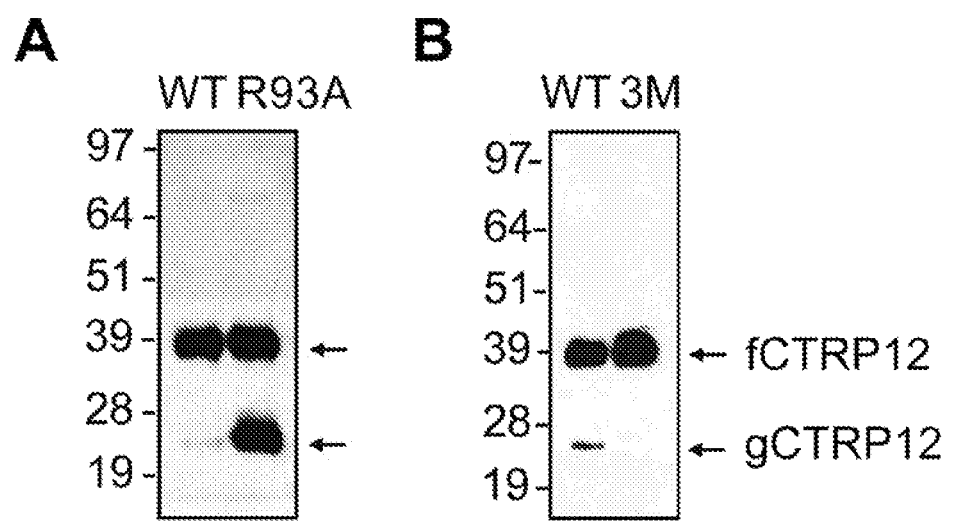
FIG. 20 depicts CTRP12 mutants with enhanced or suppressed cleavage. In 20A Immunoblot analysis of secreted wild-type (WT) CTRP12 and its R93A mutant. B, Immunoblot analysis of secreted WT CTRP12 and its triple mutant (K90A, K91A, R93A; designated as 3M).

Mutations that enhance or suppresses cleavage. Amino acids surrounding a proteolytic cleavage site influence the specificity of endopeptidase cleavage. Interestingly, when the charged Arg-93 (at the P2' position of CTRP12) was substituted with Ala, the R93A mutant exhibited enhanced cleavage compared to wild-type (WT) CTRP12 (FIG. 20A). In contrast, proteolytic cleavage was largely abolished as expected when the polybasic residues "KKXR" were converted to Ala, as in the triple mutant, K90A; K91A; R93A (3M) (FIG. 20B). These results suggest that the two mutants can be used to investigate the functional significance of proteolytic cleavage.

Example 11

Figure 21:
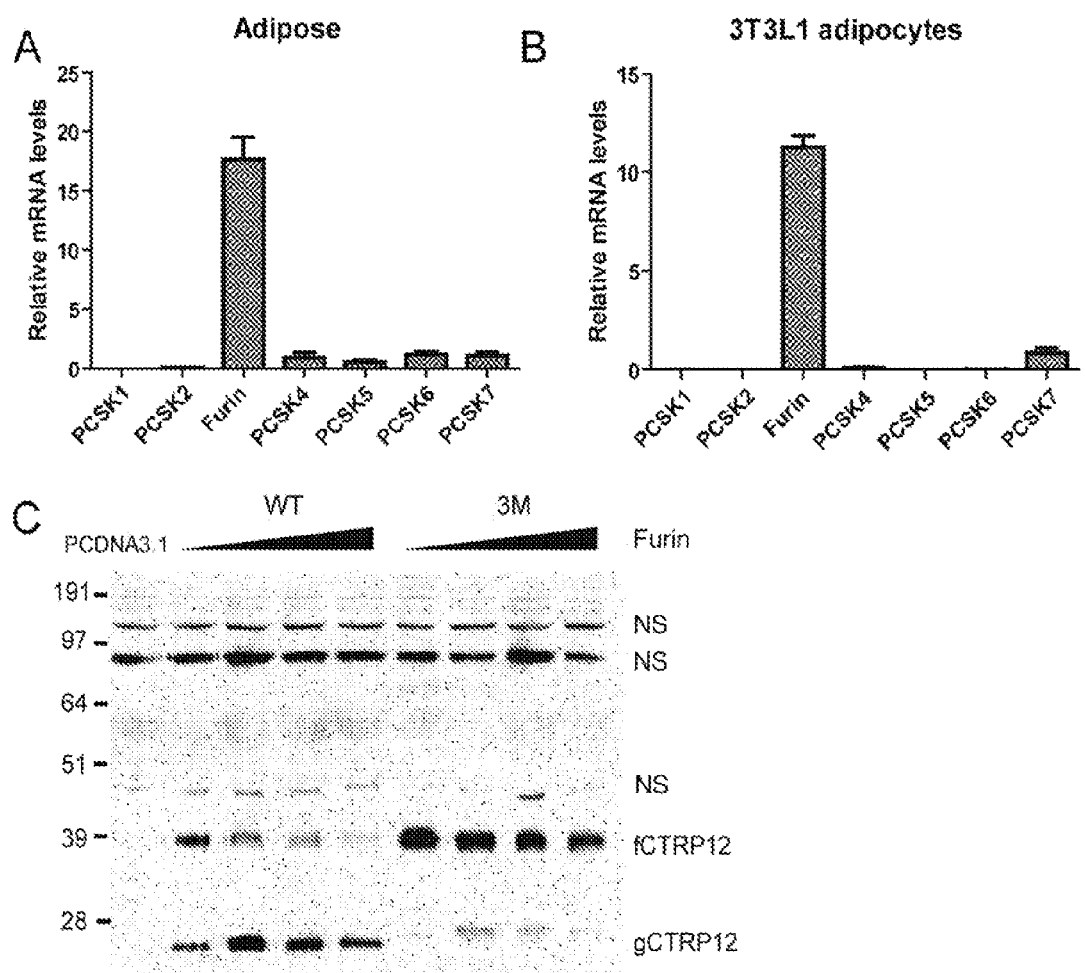
FIG. 21 shows that PCSK3/furin cleaves fCTRP12 at the $K^{90}KSR$ motif 21A-21B depicts the relative mRNA levels of different pro-protein convertase (PC) family members (PCSK1-7) in epididymal fat tissue (n=10) (21A) and in differentiated 3T3-L1 adipocytes (n=6) (21B). All quantitative real-time PCR values were normalized to 18 S rRNA. The expression of PCSK1 was set to 1 and expression levels of other PC family members were normalized against PCSK1. 21C shows HEK 293T cells were co-transfected with wild-type (WT) CTRP12 or its 3M mutant construct and an increasing amount of plasmid DNA encoding PCSK3/furin (lanes 2-9). As control, HEK 293T cells were also transfected with empty pcDNA3.1 plasmid (lane 1). Shown is the immublot analysis of secreted WT or 3M mutant protein found in the supernatant of transfected cells. NS, non-specific band.

CTRP12 is cleaved by a member of the proprotein convertases. Endoproteolytic cleavage of CTRP12 after a basic residue suggests the involvement of serine proteases of the proprotein convertase (PC) family. Nine members compose the PC family (designated as PCSK1-9). Only the first seven members cleave C-terminal to a single (K/R) or pairs of basic residues [(K/R)(K/R)]. Of these, PCSK3/furin shows the highest expression in adipose tissue and differentiated mouse 3T3-L1 adipocytes (FIG. 21A, B). Co-expression of PCSK3/furin with WT CTRP12 in HEK 293T cells led to enhanced cleavage of the protein in a dose-dependent manner: increasing the expression of furin led to a proportional reduction in fCTRP12 and a simultaneous increase in cleaved gCTRP12 secreted into the conditioned medium (FIG. 21C). In contrast, co-expression of PCSK3/furin with the triple mutant (3M) largely abolished proteolytic cleavage of CTRP12, confirming that the cleavage site of furin is indeed at the polybasic "KKSR" motif (FIG. 21C). Minor residual cleavage of the 3M mutant may be the result of cleavage at non-preferred basic residues (e.g., Arg-74 and Arg-75) adjacent to the Arg-91 by furin or other members of the PC family expressed at low levels in HEK 293T cells. Consistent with this, residual gCTRP12 generated from the 3M mutant had a slightly larger apparent molecular weight relative to gCTRP12 generated from the WT protein (FIG. 21C). This supports minor cleavage of the 3M mutant upstream of the preferred furin cleavage site at Lys-91. Together, these results indicate that PCSK3/furin is likely the endopeptidase of the proprotein convertase family that can generate the naturally occurring gCTRP12 isoform in adipocytes All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating Type 2 diabetes mellitus in a human subject in need thereof, comprising administering to the subject in an effective amount of a C1Q/TNF-related Protein 12 (CTRP12) polypeptide having an amino acid sequence selected from the group consisting of SEQ ID NOs: 1 and 2 or a functional peptide portion thereof, wherein the peptide portion is the C-terminal active fragment.

2. The method of claim 1, wherein the C-terminal active fragment consists of amino acids 92-308 of SEQ ID NOS: 1 or 2, said functional peptide portion thereof having an activity selected from the group consisting of:
   a) reduction of blood glucose level;
   b) improvement of insulin sensitivity;
   c) normalization of hyperglycemia;
   d) suppression of gluconeogenesis;
   e) promotion of glucose uptake;
   f) suppression of hepatic lipogenic program;
   g) activation of PI3K-Akt signaling pathway; and
   h) any combination of two or more of a) through g).

* * * * *